(12) United States Patent
Weber et al.

(10) Patent No.: US 9,574,221 B2
(45) Date of Patent: Feb. 21, 2017

(54) METHOD FOR THE DETERMINATION OF THE CONCENTRATION OF VITAMIN B6 IN A SAMPLE

(75) Inventors: Jakob Weber, Reinach (CH); Lara Hasan, Allschwil (CH); Thomas Jermann, Roeschenz (CH); Michel-Angelo Sciotti, Frick (CH); Daniel Gygax, Himmelried (CH); Andre Scholer, Bottmingen (CH)

(73) Assignee: BÜHLMANN LABORATORIES AG (CH)

( * ) Notice: Subject to any disclaimer, the term of this patent is extended or adjusted under 35 U.S.C. 154(b) by 305 days.

(21) Appl. No.: 14/124,958

(22) PCT Filed: Jun. 11, 2012

(86) PCT No.: PCT/EP2012/060965
§ 371 (c)(1),
(2), (4) Date: Apr. 16, 2014

(87) PCT Pub. No.: WO2012/168470
PCT Pub. Date: Dec. 13, 2012

(65) Prior Publication Data
US 2014/0308691 A1    Oct. 16, 2014

(30) Foreign Application Priority Data
Jun. 9, 2011   (EP) .................................... 11169345

(51) Int. Cl.
| | | |
|---|---|---|
| *C12Q 1/48* | (2006.01) | |
| *C12Q 1/28* | (2006.01) | |
| *G01N 33/82* | (2006.01) | |
| *C12Q 1/527* | (2006.01) | |
| *C12Q 1/26* | (2006.01) | |

(52) U.S. Cl.
CPC ............... *C12Q 1/48* (2013.01); *C12Q 1/26* (2013.01); *C12Q 1/28* (2013.01); *C12Q 1/527* (2013.01); *G01N 33/82* (2013.01); *G01N 2333/90238* (2013.01); *G01N 2333/988* (2013.01)

(58) Field of Classification Search
CPC . C12Q 1/26; C12Q 1/527; C12Q 1/48; C12Q 1/28; G01N 33/82; G01N 2333/988; G01N 2333/90238
USPC .......................................................... 435/15
See application file for complete search history.

(56) References Cited

U.S. PATENT DOCUMENTS

| 4,059,407 A | * | 11/1977 | Hochstrasser | ....... | G01N 33/528 422/424 |
|---|---|---|---|---|---|
| 6,426,194 B1 | | 7/2002 | Xu et al. | | |

FOREIGN PATENT DOCUMENTS

| DE | 199 25 120 A1 | 12/2000 |
|---|---|---|
| WO | WO 2008/118176 A2 | 10/2008 |

OTHER PUBLICATIONS

Bowsher et al. (1983). Decarboxylation of p-Tyrosine: A Potential Source of p-Tyramine in Mammalian Tissues. Journal of Neurochemistry, v40(4), p. 992-1002.*
Hida et al. (1998). Monoamine oxidase activity in noradrenaline neurons of the locus coeruleus of the rat. A double-labeling histochemical study. Brain Research, v814(1), p.209-212.*
Ran et al. (2006). Glutathione Peroxidase 4 Protects Cortical Neurons From Oxidative Injury and Amyloid Toxicity. Journal of Neuroscience Research, v84, p. 202-208.*
Connil et al. Identification of the Enterococcus faecalis Tyrosine Decarboxylase Operon Involved in Tyramine Production. Applied and Environmental Microbiology (2002), v68(7), p. 3537-3544.*
Fadda et al. Tyramine degradation and tyramine/histamine production by lactic acid bacteria and Kocuria strains. Biotechnology Letters (2001), v23, p. 2015-2019.*
Graslund et al. Protein production and purification. Nature Methods (2008), v5(2), p. 135-146.*
Han et al. Nonradioactive enzymatic assay for plasma and serum vitamin B6. Nature Protocols (2008), v3(12), p. 1815-1819.*
Shimizu et al. Rapid Enzymatic Analysis of Plasma for Tyrosine. Clin. Chem. (1990), v36(1), p. 32-35.*
Bartley et al. PCR amplification and cloning of tyrosine decarboxylase involved in synephrine biosynthesis in Citrus. New Biotechnology (epub Apr. 18, 2010), v27(4), p. 308-316.*
Roh et al. Purification, Cloning, and Three-Dimensional Structure Prediction of Micrococcus luteus FAD-Containing Tyramine Oxidase. Biochemical and Biophysical Research Communications (2000), v268, p. 293-297.*
Ross et al. Evidence for regulartion of the NADH peroxidase gene (npr) from Enterococcus Faecalis by OxyR. FEMS Microbiology (1997), v151, p. 177-183.*
Sloger et al. Effects of Pregnancy and Lactation on Pyridoxal 5'-Phosphate in Plasma, Blood and Liver of Rats Fed Three Levels of Vitamin B-6. J. Nutr. (1980), v110, p. 1517-1524.*
Poon et al. Enzymatic Fluorometric Assay for Plasma Pyridoxal 5'-phosphate. Clin. Biochem (1991), v24, p. 149-152.*

(Continued)

*Primary Examiner* — Scott Long
*Assistant Examiner* — Sean C Barron
(74) *Attorney, Agent, or Firm* — Lerner, David, Littenberg, Krumholz & Mentlik, LLP

(57) ABSTRACT

The invention relates to methods for the determination of vitamin B6 in samples as well as to reagent compositions for assaying a sample for vitamin B6 and to a test kit suitable for carrying out the methods according to the present invention. Further, the invention relates to the use of such methods for the application to different analyzing devices such as microtiter plate readers and fully automated clinical chemistry analyzers (autoanalyzers).

17 Claims, 19 Drawing Sheets

(56) References Cited

OTHER PUBLICATIONS

Rodriguez-Rodriguez et al. Vitamin B6 status improves in overweight/obese women following a hypocaloric diet rich in breakfast cereals, and may help in maintaining fat-free mass. International Journal of Obesity (2008), p. 32, p. 1552-1558.*
Kinard et al. Electroanalysis and Biosensors in Clinical Chemistry. Encyclopedia of Analytical Chemistry (2006), p. 1-35.*
Tsuge et al. Change in Blood Levels of Vitamin B-6 derivatives in Pregnant and Lactating Rats. J. Nutr. Sci. Vitaminol. (1994), v40, p. 239-249.*
Lequeu et al., *Analytical Biochemistry*, 149:296-300 (1985).
International Search Report PCT/EP2012/060965 dated Jul. 12, 2012.
Leklem, James E, "Vitamin B6," Modern Nutrition in Health and Disease, 9th Ed., Baltimore: Williams and Wilkins, 1999, pp. 413-421.
Bernstein, Allan L., "Vitamin B6 in Clinical Neurology," Annals New York Academy of Sciences, 1990, pp. 250-260.
Copeland, et al., "Pyridoxine in Carpal Tunnel Syndrome," The Annals of Pharmacotherapy, vol. 28, Sep. 1994, pp. 1042-1044.
Weir et al., "Depression of Vitamin B6 Levels Due to Theophylline," Annals of Allergy, vol. 65, Jul. 1990, pp. 59-62.
Percudani et al., "A Genomic Overview of Pyridoxal-Phosphate-Dependent Enzymes," EMBO, vol. 4, o. 9, 2003Reports, pp. 850-854.
Schwammenthal, et al., "Homocysteine, B-Vitamin Supplementation, and Stroke Prevention: from Observational to Interventional Trials," The Lancet Neurology, vol. 3, Aug. 2004, pp. 493-495.
Folsom, et al., "Prospective Study of Coronary Heart Disease Incidence in Relation to Fasting Total Homocysteine, Related to Genetic Polyorphisms, and B Vitamins," Circulation, 1998, pp. 204-210.
Torres-Sequieros, et al., "Analysis of Fluorescent Vitamins Riboflavin and Pyiridoxine in Beverages with Added Vitamins," Chromatographia, 2001, vol. 53, Suppl. pp. S-236-239.
Argoudelis, Chris J., "Simple High-Performance Liquid Chromatographic Method for the Determination of All Seven Vitamin B6-related Compounds," Journal of Chromaography, 1997, vol. 790, pp. 83-91.
Gregory III, et al., "Bioavailability of Pyridoxine-5-β-D-Glucoside Determined in Humans by Stable-Isotopic Methods 1,2,3," The Journal of Nutrition, 1991, vol. 121, pp. 177-186.
Borsch, Chrisian, "Optimierte HPLC-Analytik zur Bestimmung der Bioverfügbarkeit von Freiem and Gebundenem Vitamin B6 in Physiologischen Konzentrationen beim Menschen," PhD Thesis, Geissen 2002, pp. 1-214.
Richterich T., Colombo J.P. Klinische Chemie 4th ed. 1978, S. Karger, Basel, pp. 319-328.

* cited by examiner

- REA = Radio-Enzymatic Assay
- Indirect Assay (measurand is ³H-Tyramine)

METHOD FOR THE DETERMINATION OF THE CONCENTRATION OF VITAMIN B6 IN A SAMPLE

CROSS-REFERENCE TO RELATED APPLICATIONS

This application is a U.S. National Stage application, claiming benefit under 35 U.S.C. §§120 and 365 of International Application No. PCT/EP2012/060965, filed Jun. 11, 2012, and claiming benefit under 35 U.S.C. §119 of European Application No. 11 169 345.3, filed Jun. 9, 2011, the entire disclosures of both prior applications being incorporated herein by reference in their entirety.

BACKGROUND

The invention relates to methods for the determination of vitamin B6 in samples as well as to reagent compositions for assaying a sample for vitamin B6 and to a test kit suitable for carrying out the methods according to the present invention. Further the invention relates to the use of such methods for the application to different analyzing devices such as microtiter plate readers and fully automated clinical chemistry analyzers (autoanalyzers).

Vitamin B6 is a water-soluble vitamin that exists in three major chemical forms: pyridoxine, pyridoxal and pyridoxamine. It performs a wide variety of functions in the human body and is essential to maintain a good state of health. For example, vitamin B6 is needed as a co-factor for more than 100 enzymes involved in protein metabolism. It is also essential for red blood cell metabolism, the nervous and immune systems need vitamin B6 to function efficiently and it is also needed for the conversion of the amino acid, tryptophan, to niacin (another vitamin). The body also needs vitamin B6 to generate haemoglobin, where vitamin B6 helps to increase the amount of oxygen bound to haemoglobin. In general, vitamins are important for the immune system because they promote the growth of white blood cells which directly fight against infections. In addition, it helps to maintain the health of lymphoid organs (such as thymus, spleen and so lymph nodes).

Vitamin B6 also helps to maintain blood glucose (sugar) within a normal range. When caloric intake is low, the body needs vitamin B6 to help to convert stored carbohydrates or other nutrients to glucose to maintain normal blood sugar levels. A shortage of vitamin B6 will limit these functions.

According to Leklem (Modern Nutrition in Health and Disease, 9$^{th}$ ed., Baltimore: Williams and Wilkins, 1999: 413-421) vitamin B6 is needed for the synthesis of neural transmitters such as serotonin and dopamine. Bernstein (Ann. NY Acad. Sci. 1990; 585:250-60) discovered that these neural transmitters are required for normal nerve cell communication. It is also described that there is a relationship between vitamin B6 concentrations and a wide variety of neurologic disorders such as seizures, chronic pain, depression, headache and Parkinson's disease.

Vitamin B6 was also recommended to treat carpal tunnel syndrome (Copeland and Stoukides, Ann Pharmacother 1994; 28:1042-4). It is still advised to take 100 to 200 milligrams of vitamin B6 per day in cases of carpal tunnel syndrome.

Vitamin B6 has also become a popular remedy for treating the discomforts associated with premenstrual syndrome (PMS).

Vitamin B6 is a water-soluble compound that was discovered in the 1930s during nutrition studies on rats. The vitamin was named pyridoxine to indicate its structural homology to pyridine. Later it was shown that vitamin B6 could exist in two other slightly different chemical forms, termed pyridoxal and pyridoxamine. All three forms of vitamin B6 are precursors of the biologically active compound known as pyridoxal-5'-phosphate (PLP).

PLP acts as a coenzyme in all transamination reactions, and in some decarboxylation and deamination reactions of amino acids. The aldehyde group of PLP forms a Schiff-base linkage with the s-amino group of a specific lysine group of the aminotransferase enzyme. The α-amino group of the amino acid substrate displaces the s-amino of the lysine residue in the active site of the enzymes. The resulting aldimine is deprotonated to become a quinoid intermediate, which in turn accepts a proton at a different position on the molecule to become a ketimine. The resulting ketimine is hydrolysed so that the amino group remains on the complex.

PLP is also active in the condensation reaction towards heme synthesis.

Such versatility arises from the ability of PLP to covalently bind the substrate, and then to act as an electrophilic catalyst, thereby stabilizing types of carbanionic reaction intermediates. Overall, the Enzyme Commission (www-.chem.qmul.ac.uk/iubmb/enzyme) has catalogued more than 140 PLP-dependent activities.

Vitamin B6 is found in a wide variety of foods including fortified cereals, beans, meat, poultry, fish and some vegetables.

Clinical signs of vitamin B6 deficiency are rare in young people of industrialized nations. Many older individuals, however, have low blood levels of vitamin B6 which may suggest a marginal or sub-optimal vitamin B6 nutritional status. Vitamin B6 deficiency can occur in individuals with poor quality diets that are deficient in many nutrients. Symptoms occur during later stages of deficiency, when intake has been very low for an extended time. Signs of vitamin B6 deficiency include dermatitis (skin inflammation), glossitis (a sore tongue), depression, confusion and convulsions. Vitamin B6 deficiency can also cause anaemia. Some of these symptoms can also result from a variety of other medical conditions different from vitamin B6 deficiency. Therefore, it is important to have a physician evaluating these symptoms, including the determination of the Vitamin B6 status, so that appropriate medical care can be given (Institute of Medicine, National Academy Press, Washington, D.C., 1998).

Individuals with a poor quality diet or an inadequate vitamin B6 intake over an extended period may benefit from taking a vitamin B6 supplement, if they are unable to increase their dietary intake of vitamin B6. Alcoholics and older adults often show low vitamin B6 concentrations because of the limited variation of their diet. Alcohol also promotes the destruction and loss of vitamin B6 from the body.

Asthmatic children treated with the drug, theophylline, may need to take a vitamin B6 supplement (Weir et al, Ann. Allergy 1990; 65:59-62). Theophylline decreases vitamin B6 levels and theophylline-induced seizures have been linked to low body stores of the vitamin.

Classical syndromes for vitamin B6 deficiency are also seborrheic dermatitis-like eruption, atrophic glossitis with eruption, atrophic glossitis with ulceration, angular cheilitis, conjunctivitis, intertrigo and neurologic symptoms of somnolence, confusion and neuropathy.

Vitamin B6 is also a co-factor for glutamic acid decarboxylase, an enzyme that converts glutamate to GABA. Therefore, the concurrent increase of the excitatory neurotransmitter, glutamate, and the decrease of the inhibitory neurotransmitter, GABA, resulting from vitamin B6 deficiency potentially manifesting in seizures.

The term vitamin B6 includes several related molecules of which the active entity is pyridoxal-5'-phosphate (PLP). PLP serves as a coenzyme for many enzymes, primarily transferases, lyases and isomerases (Percudani R, Peracchi A. EMBO Rep 2003; 4(9):850-4). This predominantly prokaryotic cofactor is essential for eukaryotes for basic cell metabolism. Well known is the requirement of PLP as a coenzyme for cystathione-β-synthase (CBS), catalyzing the important step of the conversion of homocysteine to cysteine. A deficiency of PLP or vitamin B6 leads to increased levels of CBS substrates, including elevated homocysteine. Higher homocysteine levels correlate with higher risk for cardiovascular diseases, in particular an elevated risk for heart attack (Schwammenthal Y, Tanne D. Lancet Neurol 2004; 3(8):493-5). In a prominent study low blood PLP concentrations have been shown to be an independent risk factor for coronary heart disease (Folsom A R, et al. Circulation 1998; 98:204-10).

An overdose of pyridoxine can cause a temporary loss of certain nerves such as the proprioceptory nerves; causing a feeling of disembodiment, common with the loss of proprioception. This condition is reversible when supplementation is stopped.

Although vitamin B6 is a water-soluble vitamin and is excreted in the urine, very high doses of pyridoxine over long periods of time may result in painful neurological symptoms known as sensory neuropathy. Symptoms include pain and numbness of the extremities, and in severe cases difficulty in walking. Sensory neuropathy typically develops at doses of pyridoxine in excess of 1,000 mg per day. However, there have been a few case reports of individuals who developed sensory neuropathies at doses of less than 500 milligrams daily over a period of months. In order to prevent sensory neuropathy in virtually all individuals, the Food and Nutrition Board of the Institute of Medicine of the Unites States of Amerika, Wash., set the tolerable upper intake level (UL) for pyridoxine at 100 milligrams per day for adults. Because placebo-controlled studies have generally failed to show therapeutic benefits of high doses of pyridoxine, there are only a few indications to exceed the UL of 100 milligrams per day. Studies have shown that in the case of individuals diagnosed with autism, high doses of vitamin B6 given with magnesium have been extremely beneficial.

Measurement of the concentration of vitamin B6 is therefore an important diagnostic tool. It has been carried out in the past by several different testing methods such as biologically deductive, biochemical and physico-chemical methods.

Methods using High Pressure Liquid Chromatography (HPLC) analysis such as developed by Torres-Sequeiros et al (Chromatografia 2001; 53:S236-9) and Argoudelis C. J. (Chromatografia 1997; 790:83-91) do have the advantage that the determination of vitamin B6 is rapidly and practicably realizable, however, the detection limit often does not exceed 6 micromols/liter which makes them unsuitable for the determination of physiological concentrations. Moreover, the equipment needed is costly and their maintenance can be time-consuming. The hand-ling of HPLC analyzers requires well trained and qualified technicians.

In this context, there is also an example referred to a method using the commercially available ClinRep® Komplettkit "Vitamin B6 in Plasma/Vollblut" (RECIPE CHEMICALS+INSTRUMENTS GmbH) whereas the sample (e.g. plasma or blood) is first treated with a protein precipitation reagent followed by HPLC analysis of the supernatant, which also makes this method costly and involves the handling by highly qualified personel. Further, a similar test-kit suitable for HPLC analysis is available from Chromsystems GmbH, Germany (www.chromsystems.com).

Further, the U.S. Pat. No. 6,426,194 B1 discloses a method for quantification of PLP in biological samples. This method comprises the reaction of samples with the apoenzyme form of a PLP-requiring-enzyme which can generate a product when PLP is present, preferably one that is determinable by colorimetry or fluorescence. Apoenzymes as used in the U.S. Pat. No. 6,426,194 B1 are homocysteine/methionine alpha-gamma lyases, which have been depleted of PLP usually associated with them. This method does not involve the disadvantages regarding costs and specifically trained staff as compared to methods requiring HPLC, but it may lead to poor and imprecise results, particularly in the pathologically low range and the lower normal range below approximately 30 to 50 nanomols/liter.

Another well established method known within the state of the art has been developed by the applicant (www.buhlmannlabs.ch; product "RK-VB6"). This method relates to radio-enzymatic determination of the vitamin B6 concentration in a sample. In this method, $^3$H-tyrosine is decarboxylated by the vitamin B6 dependent enzyme, tyrosine apodecarboxylase (Y-apoDC) from Streptococcus faecalis, to $^3$H-tyramine. The activity of tyrosine apodecarboxylase is quantitatively dependent on the amount of pyridoxal-5'-phosphate (PLP) present in the reaction mixture. The $^3$H-tyramine thus produced is selectively extracted into the scintillation cocktail (the excess of $^3$H-tyrosine remains in the aqueous phase) and can be measured by liquid scintillation counting. This method is very sensitive (down to 2 nanomols/liter) and reproducible in the determination of Vitamin B6 in a wide variety of sample materials.

A further example method was reported by Gregory et al (J. Nutr. 1991; 121:177-86). This method was carried out by using deuterium-labelled pyridoxine or pyridoxine-β-glucoside.

However, the use of radioactive compounds in the latter two methods also has many disadvantages. Extensive safety precautions such as use of lead shielding and special waste treatment procedures must be undertaken in their storage, use and disposal. Expensive equipment is needed for radioactive counting. The radioactive decay of the isotopes used does not only reduce the amount of radioactivity available for detection over time, but may also initiate chemical reactions that damage the remaining reagents reducing sensitivity further. Thus, the storage of suitable reagents is limited to several months. In addition, these methods are not automatable.

Further, Mass Spectroscopy (MS) has been used for the determination of vitamin B6. It has, however, been found that up to date such methods are not suitable for practice-oriented serial measurements due to imprecise quantification (Borsch, Dissertation [PhD Thesis]: "Optimierte HPLC-Analytik zur Bestimmung der Bioverfügbarkeit von freiem and gebundenem Vitamin B6 in physiologischen Konzentrationen beim Menschen", Giessen 2002).

As a result of the disadvantages of the methods already known within the art, there is a need for other determination methods of vitamin B6, which allow a very precise determination but show less disadvantages associated with the methods already known. Further, such a method should be rapid and easily practicable, without the need of too costly equipment and highly qualified staff. Finally there is a need for a method which is also suitable for a commercially available kit with sufficient component stability.

SUMMARY

Unexpectedly it was found that the quantity of vitamin B6 in a sample can easily be determined with a very high sensitivity by the method of the present invention. Surprisingly, it is possible to obtain results comparable to the radioactive determination method of the applicant by developing a new, non-radioactive method comprising an enzymatic cascade system and measuring a simply detectable end-product.

Moreover, the method according to the present invention is automatable and compatible with autoanalyzers as used in the field of clinical chemistry. Finally, the method according to the present invention constitutes a rapid assay format.

The present invention therefore provides. A method to determine the concentration of vitamin B6 (pyridoxal-5'-phosphate, PLP) in a sample, comprising the steps of
 a) incubation of the sample with at least one PLP-dependent enzyme,
 b) contacting the PLP-dependent enzyme(s) from step a) with tyrosine,
 c) enzymatic conversion of the tyrosine to tyramine,
 d) enzymatic conversion of the tyramine resulting from step c) and hydrogen peroxide,
 e) enzymatic conversion of at least one indicator substrate and the hydrogen peroxide of step d) to a detectable compound,
 f) measuring the quantity of the absorbing compound of step e) and
 g) correlating the measured quantity of step f) with the concentration of vitamin B6 (pyridoxal-5'-phosphate, PLP) in the sample.

The invention further provides a composition for assaying a sample for vitamin B6 (pyridoxal-5'-phosphate, PLP), comprising the following components:
 a) a PLP-dependent enzyme capable of the conversion of tyrosine to tyramine,
 b) tyrosine,
 c) an enzyme capable of the conversion of tyramine to hydrogen peroxide at least one other product,
 d) an enzyme capable of the conversion of at least one indicator substrate to a detectable compound in the presence of hydrogen peroxide.

Moreover, the present invention additionally includes a test kit, suitable for performing the measurements with the present invention.

The invention also relates to the use of the method of the present invention for application to a microtiter plate or different clinical chemistry analyzers (autoanalyzers).

DETAILED DESCRIPTION

When the method of the invention is applied to a microtiter plate, the duration for carrying out the method is generally between 1 minute and 24 hours, preferably between 15 minutes and 4 hours and more preferred between 30 minutes and 3 hours and most preferred between 75 and 120 minutes. When the method is applied to a clinical chemistry analyzer, the duration for carrying out the method is generally between 10 seconds and 1 hour, more preferred between 1 minute and 20 minutes and most preferred between 5 and 10 minutes.

The term "vitamin B6" relates to all pyridine derivatives known within the state of the art such as

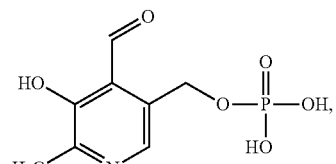

pyridoxal-5'-phospate (PLP)

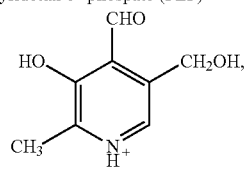

pyridoxal

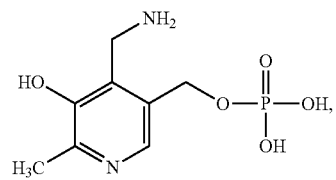

pyridoxamine-5'-phospate

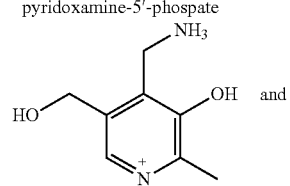

pyridoxamine

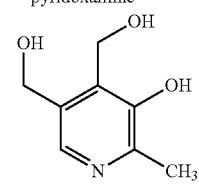

pyridoxine and the like.

It is therefore understood that all following explanations relating to vitamin B6, comprise all in the foregoing mentioned pyridine derivatives, but are not limited thereto.

The term "sample" as used in the present invention relates to all kinds of animal and human body fluids, tissue extracts, cell culture supernatant, extracts or solutions made from food or food-related products and dietary supplements.

Typical examples for samples in the sense of the present invention consisting of body fluids, are whole blood, serum, plasma, lymph, bone marrow fluid, saliva, tears, sweat, semen, cerebrospinal fluid, joint fluid, thymus solution, abdominal dropsy, amniotic fluid, cells and cell extracts, but are not limited thereto, whereas whole blood, serum and plasma are particularly suitable for the method of the present invention.

Typical examples for food-derived or food-related samples include extracts made from vegetables, meat or fish as well as cereals, flour, bread products. Moreover, in the sense of the present invention, samples can be taken from any kind of drink or food-related liquid, such as beverages, milk, tea, coffee and cocoa-containing products, but are not limited thereto.

Other typical examples are food-derived or food-related samples and liquids supplemented with vitamin B6 and its analogues, respectively, as well as the dietary supplements themselves.

The term "tyrosine" as used in the present invention refers to a substance also named 4-hydroxyphenylalanine, which is one of the 20 amino acids that are used by cells to synthesize proteins. This nonessential amino acid is usually found in large quantities in casein. Apart from being a proteogenic amino acid, tyrosine plays a special role by virtue of the phenol functionality. It occurs in proteins that are part of signal transduction processes. It functions as an acceptor of phosphate groups that are transferred by protein kinases (so-called receptor tyrosine kinases). Phosphorylation of the hydroxyl group changes the activity of the target protein.

In plants and most microorganisms tyrosine is produced via prephenate, an intermediate on the shikimate pathway. Prephenate is oxidatively decarboxylated with retention of the hydroxyl group to give phydroxyphenylpyruvate, which is transaminated using glutamate as the nitrogen source to give tyrosine and alpha-ketoglutarate.

Three isomers of tyrosine are known and are also comprised by the term "tyrosine" as used in the present invention: in addition to the common amino acid L-tyrosine, which is the para-isomer (para-Tyr, p-Tyr or 4-hydroxyphenylalanine) there are two additional isomers namely metatyrosine (m-Tyr or 3-hydroxyphenylalanine) and ortho-tyrosine (o-Tyr or 2-hydroxyphenylalanine), which occur in nature. m-Tyr and o-tyr, are isomers, which are rare, and arise through non-enzymatic free-radical hydroxylation of phenylalanine under conditions of oxidative stress.

In the method of the present invention, tyrosine is used in an amount of a 0.01 mMol/liter to 1 Mol/liter, preferably in an amount from 0.1 to 100 mMol/liter, more preferred from 0.25 to 10 mMol/liter and most preferred with an amount of 2 mMol/liter.

The term "tyramine" as used in the present invention refers to a monoamine compound, also known as 4-hydroxyphenethylamine, para-tyramine, p-tyramine, derived from the amino acid tyrosine.

In the method of the present invention tyramine is produced in an amount correlating to the amount of tyrosine used, but is also depending on other parameters such as the type and amount of enzyme used in step a) of the method of the present invention as well as pH, temperature and duration of incubation of tyrosine with the corresponding enzyme used in steps b) and c).

The enzyme used in the method of the present invention for the conversion of tyrosine to tyramine is preferably a decarboxylase. Decarboxylases (which are also termed as carboxylyases) in the sense of the present invention are carbon-carbon lyases that add or remove a carboxyl group from organic compounds. These enzymes catalyze the decarboxylation of amino acids, beta-keto acids and alpha-keto acids. In the method of the present invention a tyrosine apo-decarboxylase (EC 4.1.1.25) isolated from bacteria species or a product made by expression of a synthetic gene construct are preferably used. Alternatively, aromatic-L-amino-acid decarboxylase and phenylalanine decarboxylase may be used.

Tyrosine decarboxylase catalyzes the removal of the carboxyl group from tyrosine to produce tyramine and carbon dioxide. Vitamin B6 (pyridoxal-5'-phosphate) is thereby an obligatory coenzyme (also called co-factor). By utilizing the apoenzyme (Y-ApoDC), preferably prepared from microbial cells grown on a vitamin B6-deficient medium, vitamin B6 (PLP) can be determined. Tyrosine decarboxylase usually operates at a pH of from 3.5 to 7.5 with an optimum pH of 5.5. Operating temperature is from 4° C. to 65° C., preferably from 18° C. to 45° C. with an optimum at 37° C., whereas both parameters (temperature and pH) depend on the specific conditions of the environment, particularly the assay buffer. Inhibitors of the decarboxylase activity are heavy metals such as $Ag^+$, $Cu^{2+}$, $Fe^{2+}$, $Fe^{3+}$, $Pb^{2+}$ as well as KCN, NHOH, $N_2H_2$ and $SO^{4-}$. To obtain and/or maintain the desired pH within the reaction medium a buffer as known to a person skilled in the art can be included within step a) of the method of the present invention, such as PBS, Tris, Acetate or Citrate, but not limited thereto, whereas acetate buffer is particularly preferred. In the sense of the present invention it is also possible to use a combination of one or more buffers. The concentration of the buffer can be chosen from a concentration of from 1 mM to 2000 mM, preferably from 10 mM to 500 mM and most preferred 250 mM.

Within the method of the present invention the enzyme for converting tyrosine to tyramine is usually used in an amount of 0.01 to 10,000 U/ml, preferably in an amount of 0.1 to 1000 U/ml, more preferred from 1 to 200 U/ml and most preferred in an amount of 20 U/ml.

The term "hydrogen peroxide" ($H_2O_2$) refers to a chemical compound which is a weak acid with strong oxidizing properties. In pure forms it shows a pale blue colour but is colourless in solution. Hydrogen peroxide can decompose spontaneously into water and oxygen. It acts usually as an oxidizing agent but there are some reactions in which it acts as a reducing agent, too, releasing oxygen as a co-product. It also forms readily both inorganic and organic peroxides. Within the present invention hydrogen peroxide is part of an oxydizing reaction, which is also a colour forming reaction leading to a spectrophotometrically detectable compound.

The enzyme used within the method of the present invention to convert tyramine into a reaction product with the formation of hydrogen peroxide as a by-product is preferably an oxidase. An oxidase, in the sense of the present invention, is any enzyme that catalyzes an oxidation/reduction reaction involving molecular oxygen ($O_2$) as the electronic acceptor. In such reactions oxygen is reduced to water ($H_2O$) or hydrogen peroxide ($H_2O_7$). Oxidases are a subclass of oxidoreductases.

Within the method of the present invention monoamine oxidases (amine flavin oxidase; EC 1.4.3.4) and amine copper-containing oxidase (EC 1.4.3.6) are preferably used. The oxidase most preferably used within the method of the present invention is copper-containing oxidase, also known as tyramine oxidase. In the method of the present invention a tyramine oxidase isolated from bacteria species or a product made by expression of a synthetic gene construct are preferably used. Alternatively, diamine oxidase, aralkylamine dehydrogenase, flavin-containing monooxygenase arylsulfate sulfotransferase and tyramine N-methyltransferase may be used.

Tyramine oxidase converts specifically 1 Mol of tyramine, 1 Mol of oxygen and 1 Mol of water into 1 Mol of p-hydroxybenzylaldehyde, 1 Mol of hydrogen peroxide and 1 Mol of ammonia. The enzyme is generally working at a pH from 3.5 to pH 11 and a temperature from 15° C. to 65° C., depending on the specific conditions of the environment, particularly the assay buffer, whereas the optimum is pH 7.5 and 37° C. To obtain and maintain a pH suitable for step d) of the method of the present invention, a buffer can be included within step d). Possible, usable buffers include phosphate, maleate, chloroacetate, formate, benzoate, pyridine, piperazine, propionate, 3-N-morpholinopropanesulfonic acid (MOPS), 1,3-bis tris-hydroxymethyl)methylaminopropane (BisTRIS), tris-(hydroxymethyl)aminomethane (TRIS), tris-(hydroxymehtyl)aminomethane-maleic acid (TRIS-maleate), 2-(-tris(hydroxymethyl)methylamino)ethanesulfonic acid (TES), 1,4-piperazinebis-ethanesulfonic acid) (PIPES), 4-morpholinoethanesulfonic acid (MES), N-2-hydroxyethylpiperazine-N'-2-ethanesulfonic acid (HEPES), N,N-bis(2-hydroxyethyl)-2-aminoethanesulfonic acid (BES), N-(2-acetamido)iminodiacetic acid (ADA), N-(2-acetamido)-2-aminoethanesulfonic acid (ACES), and others known to a person skilled in the art, however TRIS-HCl is particularly preferred. The concentration of the buffer can be chosen from a concentration from 1 mM to 10 M, preferably from 50 mM to 2 M and most preferred 200 mM.

According to the method of the present invention a peroxidase is preferably used for the conversion or coupling of indicator substrates and the co-substrate hydrogen peroxide to a detectable (ie. light absorbing) compound. Peroxidases are enzymes which catalyze the oxidation via a peroxide in the following form:

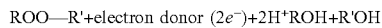

ROO—R'+electron donor $(2e^-)$+$2H^+$ROH+R'OH

For many of these enzymes the optimal co-substrate is hydrogen peroxide, while others are more active with organic hydro-peroxides such as lipid peroxides.

According to the method of the present invention the hydrogen peroxide product reacts with the component for detecting hydrogen peroxide and thus the method comprises the use of a peroxidase that selectively catalyzes a reaction between the hydrogen peroxide and at least one indicator. The peroxidase thus uses hydrogen peroxide and oxygen, which is capable of removing hydrogen atoms from various substrates. In the sense of the present invention, a suitable peroxidase may for example contain ferriprotoporphyrine, a red tymine obtained from plants. In the sense of the present invention, the peroxidase is preferably obtained from plants, preferably horseradish, but can also be obtained from animals, for example from vertebrate animals or a product made by expression of a synthetic gene construct.

For carrying out the method of the present invention horseradish peroxidase is particularly preferred. Horseradish peroxidase can use a variety of organic compounds as electron donors and acceptors. Further, it has a flexible active side and many compounds can reach the side of the reaction. Horseradish peroxidase, as used in the present invention, can be isolated from horseradish fluids (*Armoracia rusticana*) and belongs to the ferroprotoporphyrine group of peroxidases. Horseradish peroxidase, in the sense of the present invention, is a single-chain polypeptide containing four disulfide bridges. It is a glycoprotein consisting of 18% carbohydrates. The carbohydrate composition can include galactose, arabinose, xylose, fucose, manose, mannosamine and galactosamine, depending upon the specific isocine.

Horseradish peroxidase, as preferably used in the method of the present invention, is generally working in a pH range from pH 2 to pH 12, with an optimum in the range of from pH 5.5 to pH 7. In addition, horseradish peroxidase suitable for carrying out the method of the present invention, is active within a temperature range of from 15° C. to 65° C. within an optimum range of from 18° C. to 45° C., however, both parameters depend on the specific conditions of the environment, particularly the assay buffer, and can be easily adapted to a special assay by a person skilled in the art.

Horseradish peroxidase as used within the method of the present invention can be inhibited by sodium acid, cyanide, L-cystine, dichromate, ethylene-thio-urea, hydroxylamine, sulfite, vanadate, p-aminobenzol acid, $Co^{+2}$, $Cu^{+2}$, $Fe^{+3}$, $Mn^{+2}$, $Ni^{+2}$ and $Pb^{+2}$.

In the method of the present invention, an indicator suitable for the enzymatic reaction of the hydrogen peroxide to a detectable compound can be any oxidizable colour reagent consisting of a combination of 4-aminoantipyrine (4-AAP): 4-AP (4-aminophenazone), o-phenylenediamine, TMB (3,3',5,5'-tetramethylbenzidine), MBTH hydrochoride (3-methyl-2-benzothiazolinonehydrazone hydrochloride hydrate), OPD (1,2-phenylenediamine), 4-aminoantipyrine hydrochloride, 5-aminosalicylic acid, 5-amino-2-hydroxy-benzoic acid and the like] and a N,N-disubstituted aniline series compound, such as N-ethyl-N-(2-hydroxy-3-sulfopropyl)-m-toluidin (TOOS), a phenolic compound, an aniline series compound, a benzidine derivative, an o-tolidine derivative, a diphenylamine derivative, a triallylimidazole derivative, a leucomethylene blue derivative such as ABTS (2,2'-azinobis(3-ethylbenzothiazoline-6-sulfonic acid), DCBS (4-chlorophenol; 3,5-dichloro-2-hydroxybenzensulfonic acid), DCHBS (3,5-dichloro-2-hydroxybenzenesulfomc acid), DHB (3,4-dihydroxybenzoic acid), DHBS (3,5-dichloro-2-hydroxybenzenesulphonate), HBS (p-hydroxybenzene sulfonate), TBHBA (2,4,6-tribromo-3-hydroxybenzoic acid), TBHB (3-hydroxy-2,4,6-tribomobenzoic acid), HBA (4-hydroxybenzoic acid), EHSPT (N-ethyl-N-(2-hydroxy-3-sulfopropyl)-m-toluidine), Vanillic acid, Homovanillic acid, ESPA (N-ethyl-N-(3-sulfopropyl)m-anisidine), ADPS (N-Ethyl-N-(3-sulfopropyl)-3-methoxyaniline), ADOS (N-Ethyl-N-(2-hydroxy-3-sulfopropyl)-3-methoxylaniline), TOPS (N-Ethyl-N-(3-sulfopropyl)-3-methylaniline), DAOS (N-ethyl-N-(2-hydroxy-3-sulfopropyl)-3,5-dimethoxyaniline), HDAOS (N-(2-Hydroxysulfopropyl)-3,5-dimethyoxyaniline), MADB (N,N-Bis(4-sulfobutyl)-3,5-dimethylaniline), MAOS (N-Ethyl-N-(2-hydroxy-3-sulfopropyl)-3,5-dimethylaniline), TODB (N,N-Bis(4-sulfobutyl)-3-methylaniline), ALPS (N-Ethyl-N-(3-sulfopropyl)aniline), DEA (N, N-diethylaniline), dimethylaniline, 3-diethylaminotoluene, N,N-diethyl-m-toluidine, N,N-diethyl-3-methylaniline, DMA (N,N-dimethylaniline), Phenol, Aminophenol, Indophenol, 4-chlorophenol, 2,4-DCP (2,4-dichlorophenol), 2,4,6-tribromophenol, guaiacol (2-methoxyphenol), Guaiac, Leucomalachite green, Nadi reagent, Phenolphtalein, Ferrocyanide, Adrenaline, DAB (3,3'-diamino-benzidine), di-anisidine (3,3'-dimethoxybenzidine), o-tolidine (3,3'-dimethyl-(1,1'-biphenyl)-4,4'-diamine), diphenylamine, o-toluidine (1-methyl-1,2-amino-benzene), m-toluidine (3-methylbenzenamine), p-toluidine (4-aminotoluene or 4-methylaniline), benzidine (4,4'-diaminobiphenyl), catechol (1,2-dihydroxybenzene), pyrogallol (1,2,3-trihydroxybenzene), o-cresol (2-hydroxy-1-methylbenzene), m-cresol (3-Methylphenol), p-cresol (4-Methylphenol), 4-methylcatechol (1,2-dihydroxy-4-methylbenzene), 4-diphenyl sulfonic acid, 2,6-dichloroindophenol, CN (4-chloro-1-napthol), alpha-naphthol, beta-naphthol 5-ASA (5-aminosalicylic acid), AEC (3-amino-9-ethylcarbazole), 5 amino-indole, 7 amino-indole, 5 amino-benzimidazole, 7 amino-benzimidazole, 5 amino-benzothiazole, 7 amino-benzothiazole, 5 amino-benzoxazole, 7 amino-benzoxazole, 5 amino-indazole, 7 amino-indazole and the like, but they are not limited thereto.

In addition to these methods described, a method can be employed within the sense of the present invention, for quantitating $H_2O_2$ using a combined reagent of tetravalent titanium compound and 5-Br-PAPS (2-(5-bromo-2-pyridylazo)-5-(N-propyl-N-sulfopropylamino)phenol) or Xylenol Orange (3,3'-Bis[N,N-bis(carboxymethyl)aminomethyl]-o-cresolsulfonephthalein tetrasodium salt).

For stabilizing the oxidizable color reagent and its developed colour after oxidation and coloration, the presence of beta-cyclodextrine and/or a derivative thereof and of gamma-cyclodextrine and/or a derivative thereof, respectively, in the solution can be used within the method of the present invention. With respect to the concentrations of these compounds, the concentration of beta-cyclodextrine usually used in the solution is from 0.01 to 1.5 wt/vol %, that of gamma-cyclodextrine from 0.1 to 5 wt/vol % and that of gamma-cyclodextrine derivative from 1.1 to 5 wt/vol %. Mixtures of two or more of these compounds in any ratio may also be used as long as the concentrations of the compounds are within the above-mentioned ranges.

In the method of the present invention, the reaction of the hydrogen peroxide and the indicator compound(s) in step e), can be carried out at a temperature from 4° C. to 65° C., preferably from 18° C. to 50° C., more preferred from 25° C. to 40° C. and most preferred at a temperature of 37° C. Further the pH for the reaction in step e) of the present invention can be chosen between pH 2 and pH 11, preferably between pH 6 and pH 9 and most preferred at pH 7.8.

In the method of the present invention a combination and coupling, respectively, of 4-AAP and TOOS is the preferred indicator. Together with the amount of hydrogen peroxide generated in step b), a detectable compound is generated by enzymatic reaction. The detectable compound generated in the method of the present invention can be measured and quantified by any method suitable for detection and quantifying the generated compound, which is known within the state of the art.

In addition to the method of the present invention, hydrogen peroxide may be directly determined by fluorimetry or luminometry (Vogt G. PhD Thesis at Dept. of Chemistry, Technical University of Dortmund, Germany, 2000; https://eldorado.tu-dortmund.de/ . . . /3/voigtgesamt.pdf.txt) rather than indirectly as described above. Other state of the art methods to determine hydrogen peroxide are by titration with organic salt solutions (colour reactions) or as described in DE 19925120 A1.

In addition to the method of the present invention, the concentration of the resulting ammonia ($NH_3$) instead of hydrogen peroxide can be determined. Ammonia is built in an equimolar concentration as compared to hydrogen peroxide from the reaction of tyrosin to tyramine by the tyramine oxidase. The concentration of ammonia can be directly determined according to the method of Berthelot or indirectly by using glutamte dehydrogenase and NADH and by ion selective electrodes, respectively (references in Richterich R., Colombo J. P. Klinische Chemie 4th ed. 1978, S. Karger, Basel, pp. 319-328). After the deduction of the endogenous concentration of ammonia from the measured concentration, the calculated concentration of ammonia is directly proportional to the PLP concentration present in a test sample.

In the method of the present invention, possible detection modes for measuring the generated compound are absorbance, turbidimetry, nephelometry, fluorescence intensity, luminescence, time resolved fluorescence and fluorescence polarization, wherein absorbance is particularly preferred. The absorbance of the sample is preferably measured by the use of a spectrophotometer. In the sense of the present invention a spectrophotometer is a photometer (a device for measuring light intensity) that can measure intensity as a function of the color or, more specifically, of the wavelength of light. There are many kinds of possible spectrophotometers in the sense of the present invention. Among the most important distinctions used to classify them are the wavelengths they work with, the measurement techniques they use, how they acquire the spectrum and the sources of intensity variation they are designed to measure. Other important features of spectrophotometers include the spectral band-widths and linear range. Generally two different types of spectrophotometers can be used in the method of the present invention: single-beam and double-beam spectrophotometers. A double beam spectrophotometer measured the ratio of the light intensity on two different light paths and the single beam spectrophotometer measures the absolute light intensity. Although ratio measurements are easier and generally more stable single beam instruments have the advantage of a larger dynamic range.

The optical density of the sample treated after the method of the present invention can be measured at wavelengths from 200 nm to 1200 nm, preferably at a wavelength of 340 to 800 nm, more preferred at a wavelength of 450 to 650 nm and most preferred at a wavelength of 546 nm.

In the method of the present invention each step as defined within claim 1 can be carried out independently from the other and the necessary parameters can be chosen individually. Therefore each step can be carried out at a temperature, pH and with volume and for an incubation time different to the temperature, pH, volume and incubation time chosen for the other steps. In the sense of the present invention this also applies to any other parameter, which can be set up in the method of the present invention by a person skilled in the art. Examples thereof are concentration of the enzyme, compounds and/or further substances used, such as buffer substances, but are not limited thereto.

The present invention also relates to a kit suitable for carrying out the method described in the present invention. Such a test kit includes at least the following compounds: the compound tyrosine as described before, one PLP-dependent enzyme capable of the conversion of tyrosine to tyramine, one enzyme capable of the conversion of tyramine to hydrogen peroxide, an indicator substance (ie. the compound TOOS) and one enzyme capable of carrying out the reaction of hydrogen peroxide and a further indicator substance (ie. the compound 4-AAP) to form a detectable compound, but is not limited thereto. The enzyme capable of the conversion of tyrosine to tyramine is preferably a decarboxylase and most preferred tyrosine apodecarboxylase. The enzyme capable of the enzymatic conversion of tyramine to hydrogen peroxide is preferably an oxidase and most preferred tyramine oxidase. The enzyme capable of carrying out the reaction of hydrogen peroxide and at least one indicator substance is preferably a peroxidase and most preferred horseradish peroxidase. The kit may also contain optional compounds such as buffer substances, calibrator and control materials, and additional reagents such as carrier proteins, saccharides, high-molecular compounds, metal ions and gelatine compounds which were all described before in more detail, to improve the performance of the assay and stability of the reagents.

Preferably the kit contains one or more buffers such as acetate buffer, Tris-HCl and Tris-HCl containing 4-amino-anti-pyrine. The concentration of the Tris-HCl buffer is preferably between 50 and 2000 mM, more preferred 900 mM when used in combination with 4-aminoantipyrine and 100 mM when used alone. The concentration of the acetate buffer is preferably between 10 and 1000 mM and most preferred 250 mM. The concentration of 4-aminoantipyrine is preferred between 0.01 mM and 100 mM, more preferred between 0.3 mM and 10 mM and most preferred 3 mM.

In another embodiment, the kit contains calibrator material made from chemically pure PLP and control reagents made from biological samples, such as plasma or serum containing natural (endogenous) PLP in a predetermined concentration.

The present invention also relates to compositions suitable for assaying a sample of vitamin B6 comprising at least the compound tyrosine, one PLP-dependent enzyme capable of conversion of tyrosine to tyramine, one enzyme capable of the conversion of tyramine to hydrogen peroxide and one enzyme capable of carrying out the reaction of hydrogen peroxide and at least one further indicator substance to a detectable compound, but is not limited thereto. The enzyme capable of the conversion of tyrosine to tyramine is preferably a decarboxylase and most preferred tyrosine apodecarboxylase. The enzyme capable of the conversion of tyramine to hydrogen peroxide is preferably an oxidase and most preferred tyramine oxidase. The enzyme capable of carrying out the reaction of hydrogen peroxide and the indicator substance(s) to a detectable compound is preferably a peroxidase and most preferred horseradish peroxidase. All components have been described before in greater detail. Further compounds and reagents as described before in greater detail can additionally be contained in the composition.

The present invention also relates to the use of the method as described before, for the application to microtiter plate readers or to autoanalyzers.

In the sense of the present invention the microtiter plate (also microplate) is preferably a flat plate with multiple wells used as small test tubes. Each well of a microtiter plate typically holds a few up to a few hundred microliters of liquid. Microtiter plates can be handled manually but also by robots. The robots may be liquid handlers which aspirate or dispense liquid samples from and to these microplates and/or robot arms or "plate movers" which transport them between instruments. The reaction taking place in the wells of the microplate can afterwards be detected by special microplate readers. Preferably a high-intensity lamp shoots light through each well of the microtiter plate filled with liquid and the light emmitted or absorbed by the reaction taking place in each well of the microtiter plate well is quantified by a detector. Examples of suitable detection modes in the sense of the present invention are absorbance, fluorescence intensity, luminescence, time-resolved fluorescence and fluorescent polarisation, wherein absorbance is particularly preferred.

An autoanalyzer in the sense of the present invention is preferably a semi-automated or fully automated analyzer which is generally used in routine clinical chemistry laboratories and well known to the person skilled in the art. These autoanalyzers need only minimum amounts of sample (eg. from 1 to 100 microliters) and usually exhibit sample analysis times of less than ten minutes. This allows a rapid and cost-efficient turnaround in cases of high numbers of samples to be determined. In principle, the detection mode for the reaction in the tubes or vessels run on the autoanalyzers is the same as described above for the microtiter plate (readers). Examples of suitable detection modes in the sense of the present invention are absorbance, turbidimetry, nephelometry, fluorescence intensity, luminescence, time-resolved fluorescence and fluorescent polarisation, wherein absorbance is particularly preferred.

In the following, the effectiveness of the methods of the present invention for the sensitive and specific determination of vitamin B6 (PLP) are shown.

The invention in future explained by way of figures and examples which are not meant to limit the scope of the invention

$^3$H-tyrosine is decarboxylated by the PLP-dependent enzyme tyrosine apodecarboxylase (Y-apoDC) from *Streptococcus faecalis* to $^3$H-tyramine. The activity of Y-apoDC is quantitatively dependent on the amount of pyridoxal 5'-phosphate (PLP) present in the reaction mixture. The $^3$H-tyramine thus produced is selectively extracted into a scintillation cocktail (the excess of $^3$H-tyrosine remains in the aqueous phase) and can be measured by liquid scintillation counting. The amount of radioactivity (counts per minute, cpm) is directly proportional to the amount of PLP present in the sample.

Figure 1:
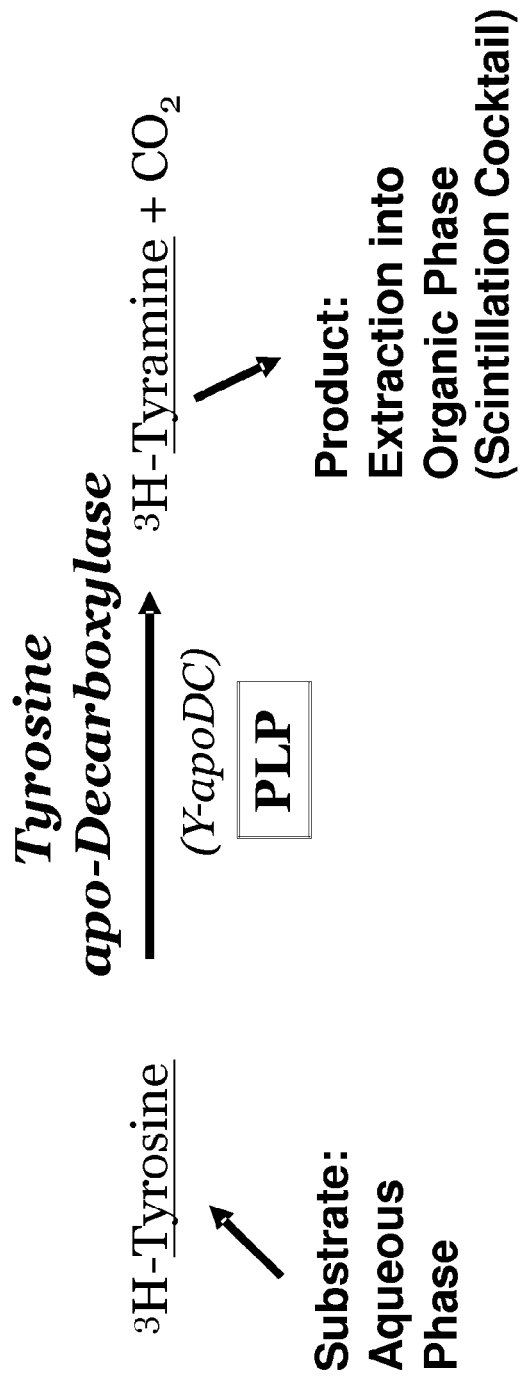
FIG. 1 shows the principle of Bühlmann Vitamin B6 radio-enzymatic assay (REA) which represents the state of the art before the present invention.
Figure 2:
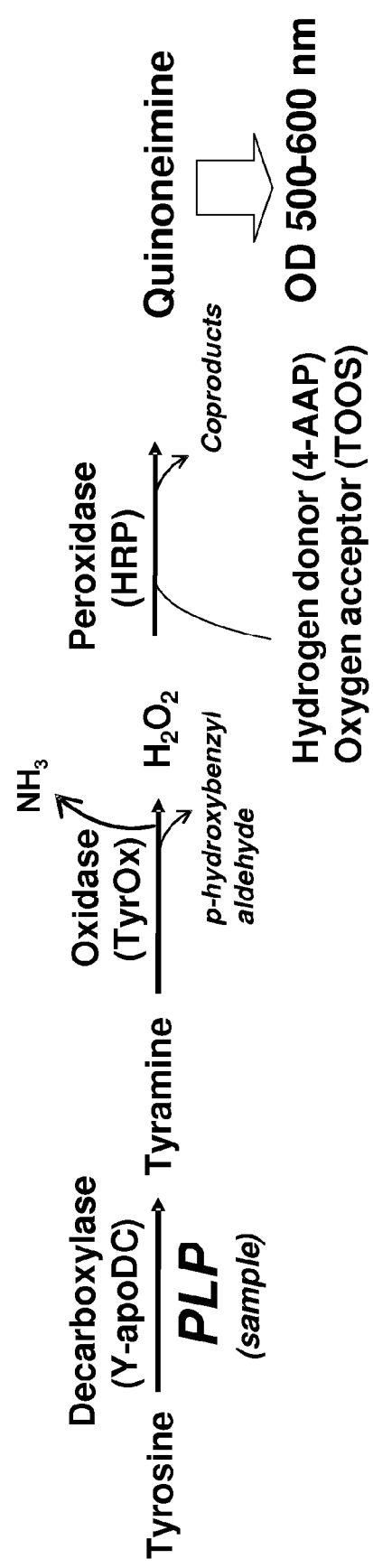

FIG. 2 shows the principle of the non-radioactive enzymatic assay of the present invention.

In the assay the tyrosine-specific enzyme, Y-apoDC (tyrosine apodecarboxylase), converts tyrosine to tyramine. The Y-apoDC activity requires PLP as cofactor. The turn-over of tyrosine to tyramine is strictly dependent on the PLP concentration present in the sample. The tyramine produced is oxidized to p-hydroxybenzylaldehyde, $NH_3$ (ammonia) and $H_2O_2$ (hydrogen peroxide) by action of TyrOx (tyramine oxidase). $H_2O_2$ catalyzes the reaction of 4-AAP (4-aminoantipyrine) and TOOS (N-ethyl-N-(2-hydroxy-3-sulfopropyl)-m-toluidine) in the presence of HRP (horseradish peroxidase) to quinoneimine (purple dye) whose absorbance is monitored between 500 and 600 nm, preferably at 546 nm. Indicated is the order of steps a) to f) of the unfused of the method of the present invention.

Figure 3:
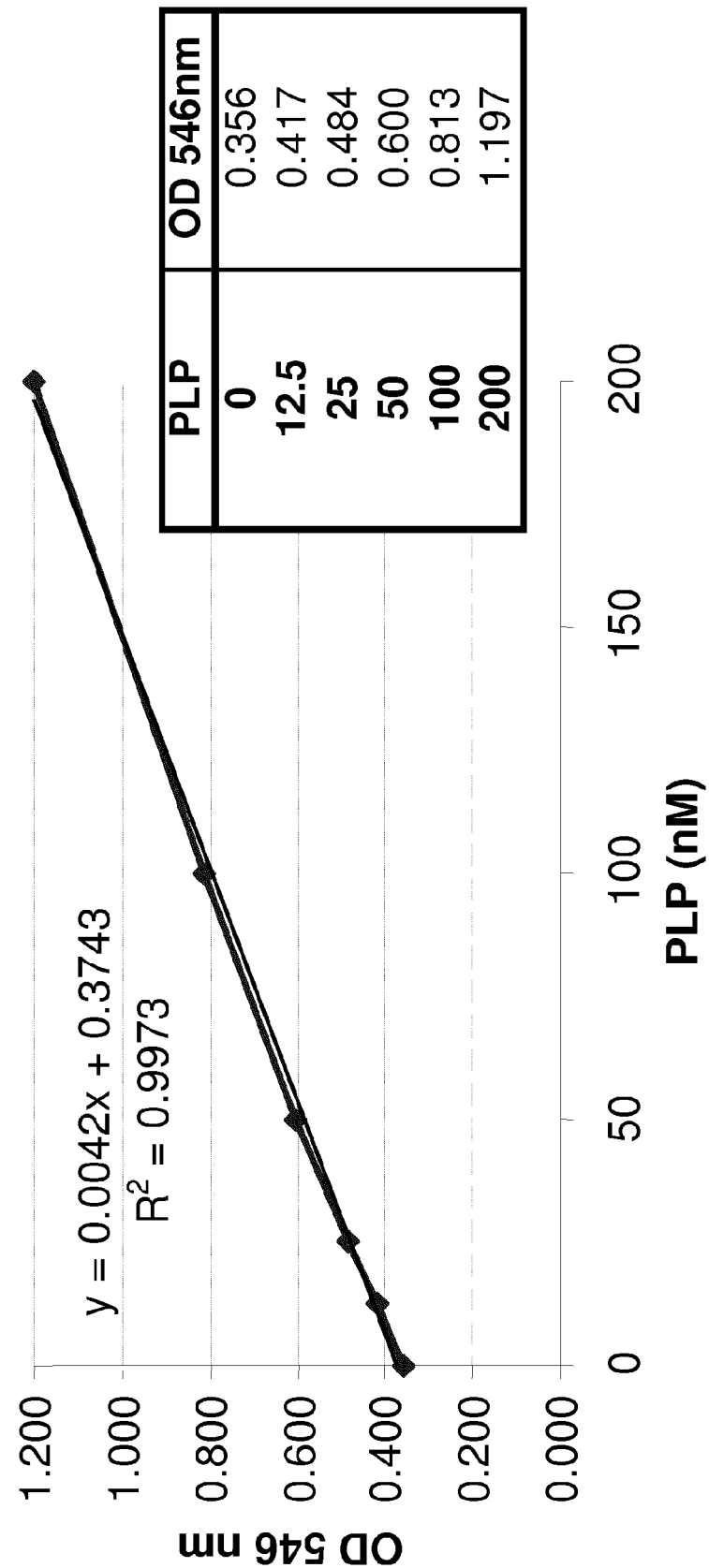

FIG. 3 shows a typical standard curve originated by determining the absorbance (OD at 546 nm) of calibrators containing various concentrations of pyridoxal-5'-phosphate (PLP) using the standard colorimetric assay protocol for microplates of the present invention as outlined in Example 1.

Figure 4:
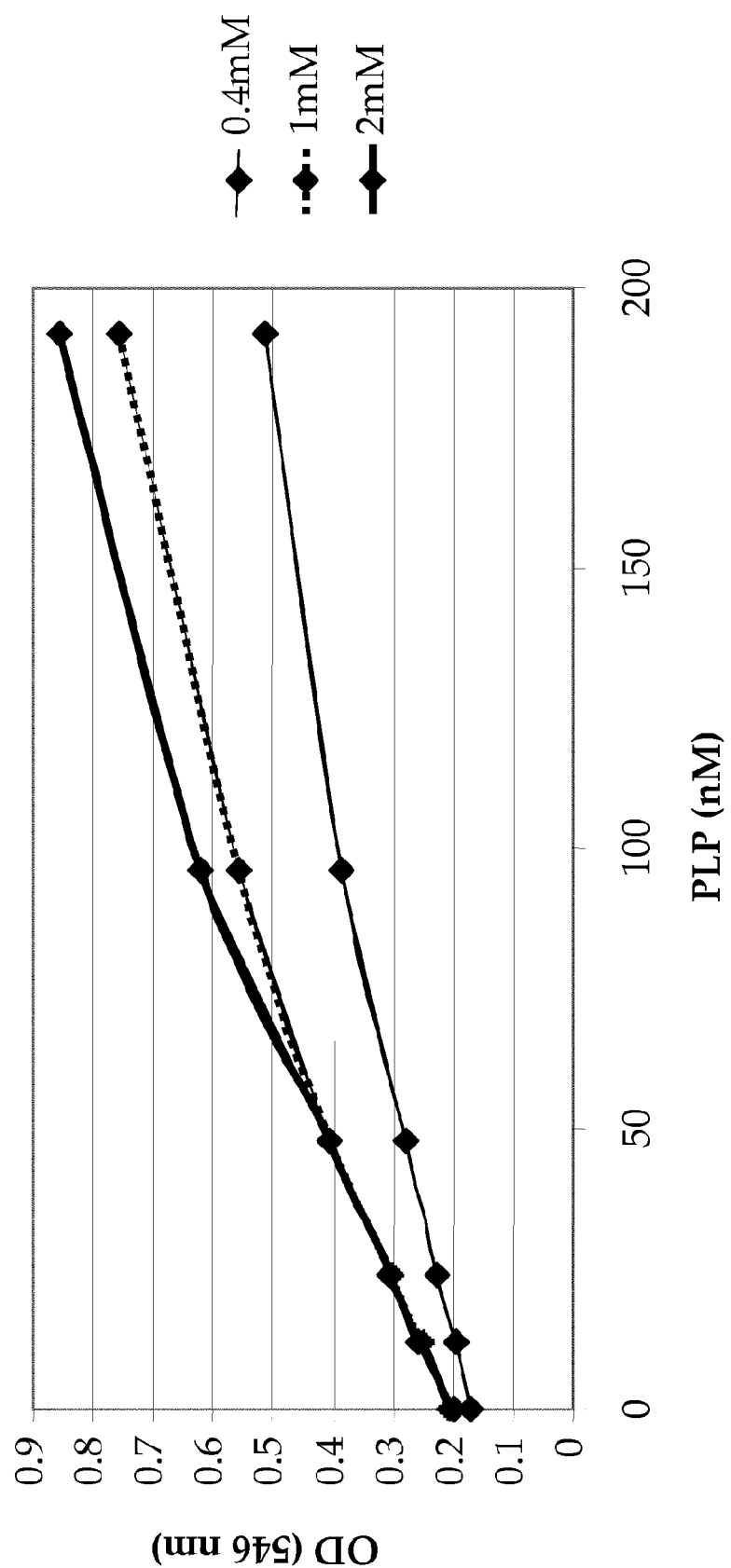

FIG. 4 shows the effects of different concentrations of L-tyrosine on the PLP standard curve.

Figure 5:
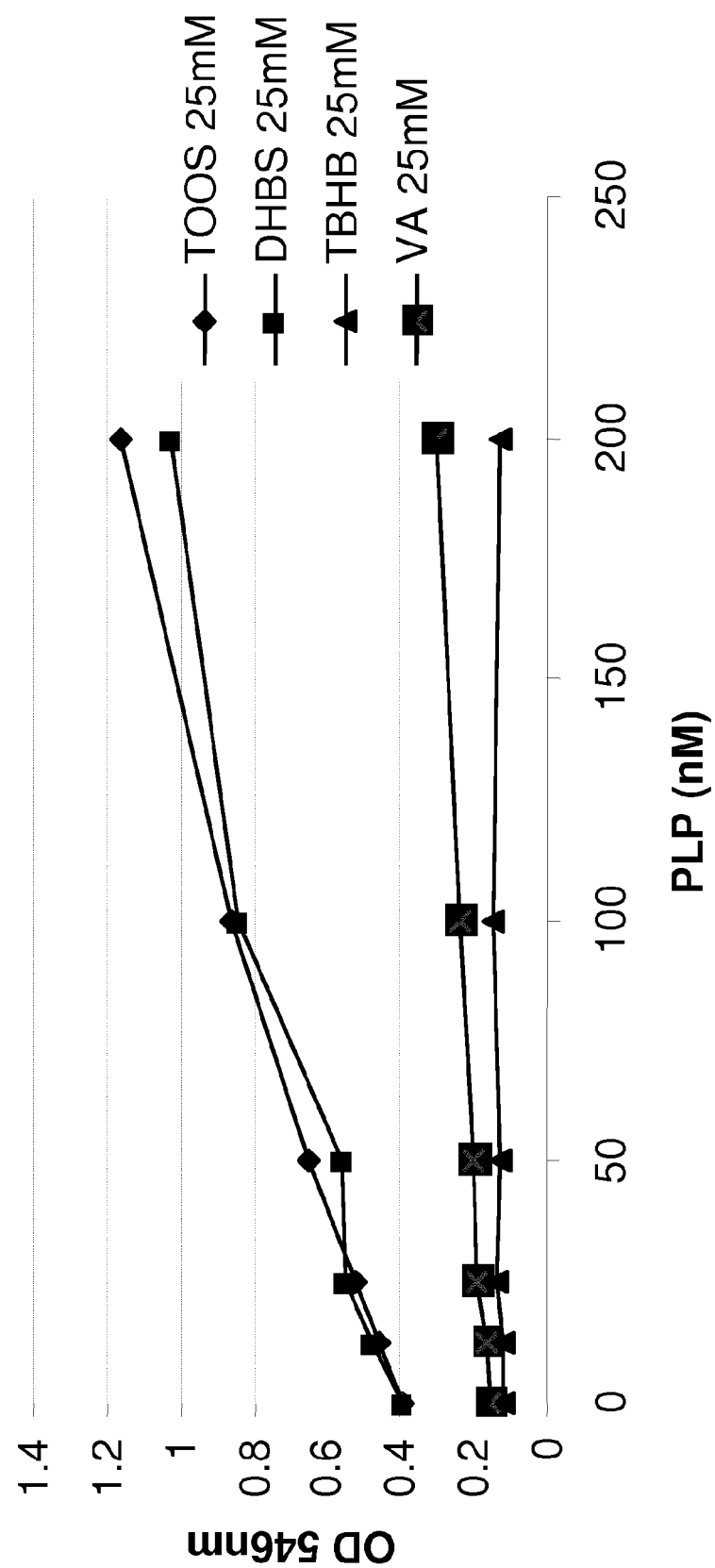

FIG. 5 shows a comparison of TOGS with the alternative compounds 3,5-Dichloro-2-hydroxybenzene sulfonic acid sodium salt (DHBS), Vanillic acid (VA) and 2,4,6-Tribromo-3-hydroxybenzoic acid (TBHB) for inducing the colour reaction.

Figure 6:
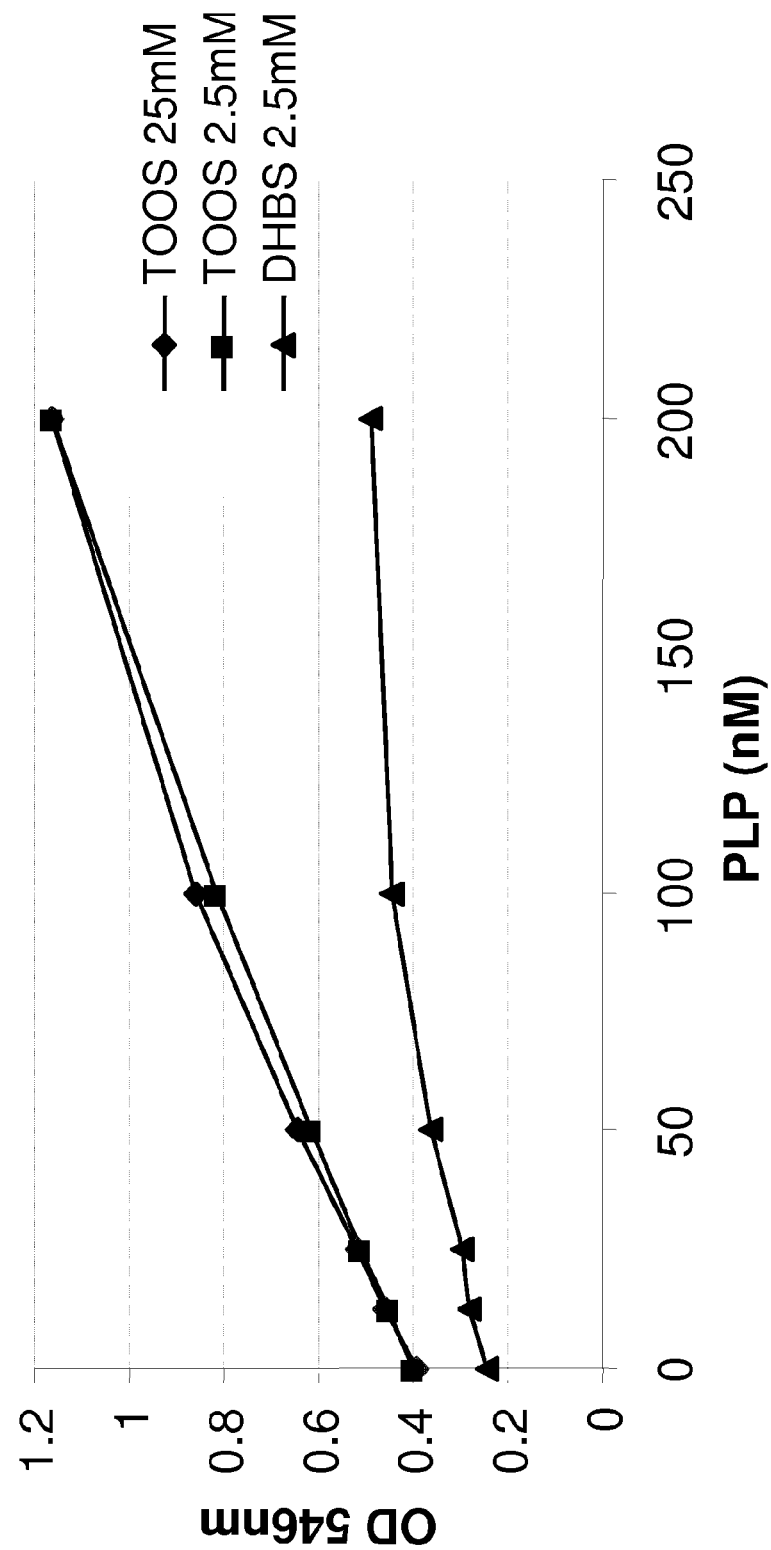

FIG. 6 shows the effects of reducing the concentration of TOOS and DHBS on the PLP standard curve.

Figure 7:
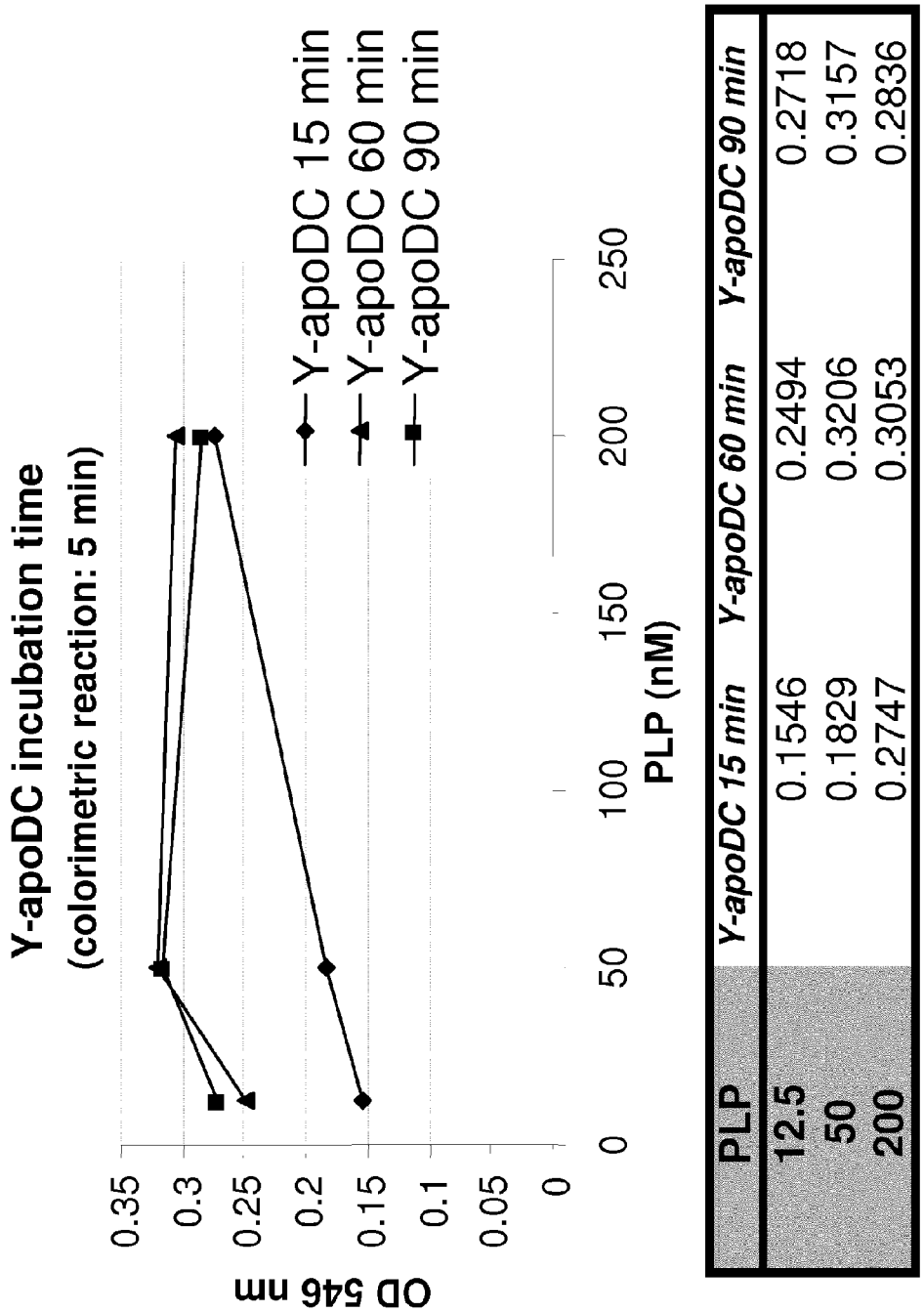

FIG. 7 shows the effect of different incubation times for the first enzyme reaction; colorimetric reaction (second enzyme reaction) fixed at 5 min.

Figure 8:
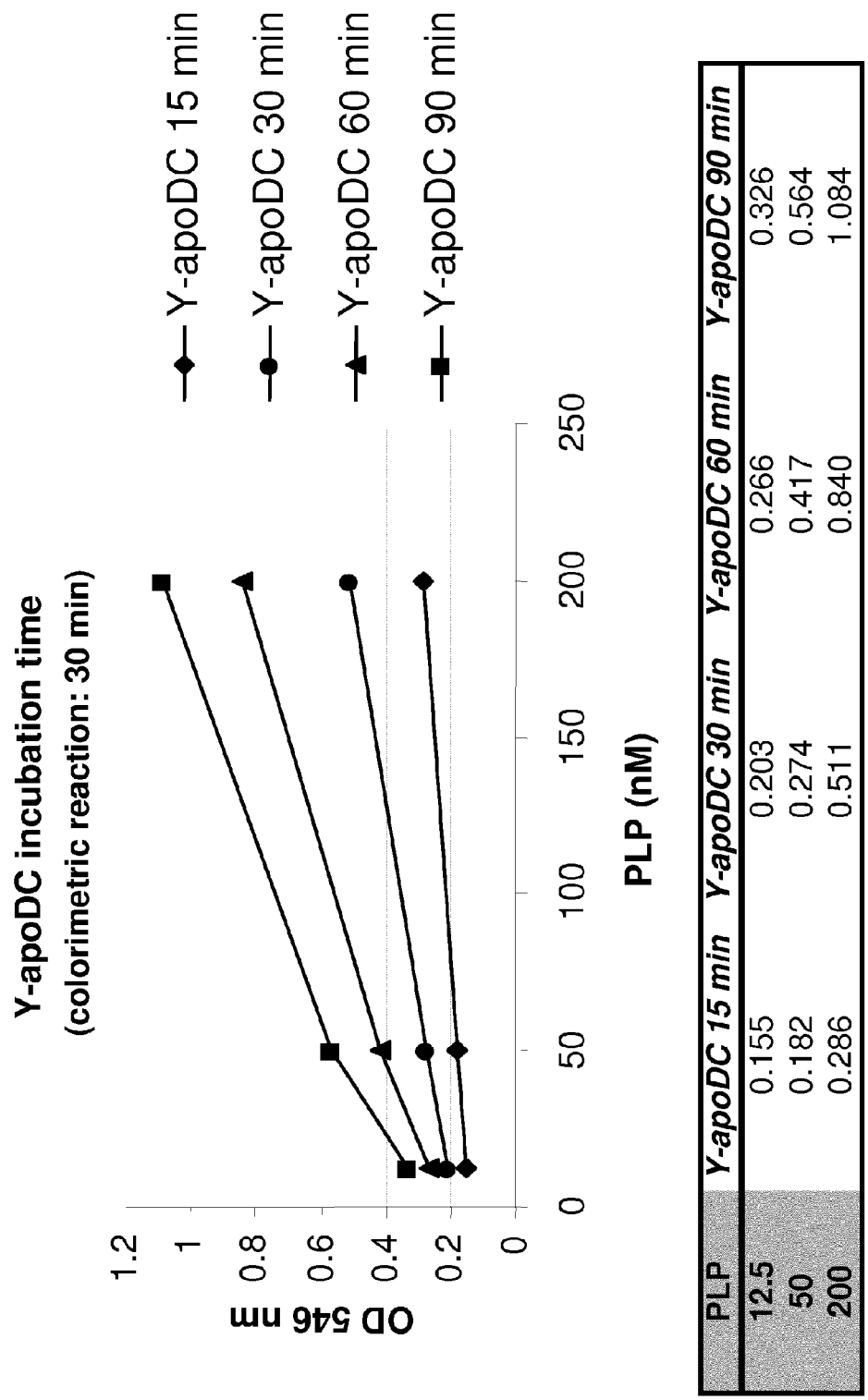

FIG. 8 shows the effect of different incubation times for the first enzyme reaction; colorimetric reaction (second enzyme reaction) fixed at 30 min.

Figure 9:
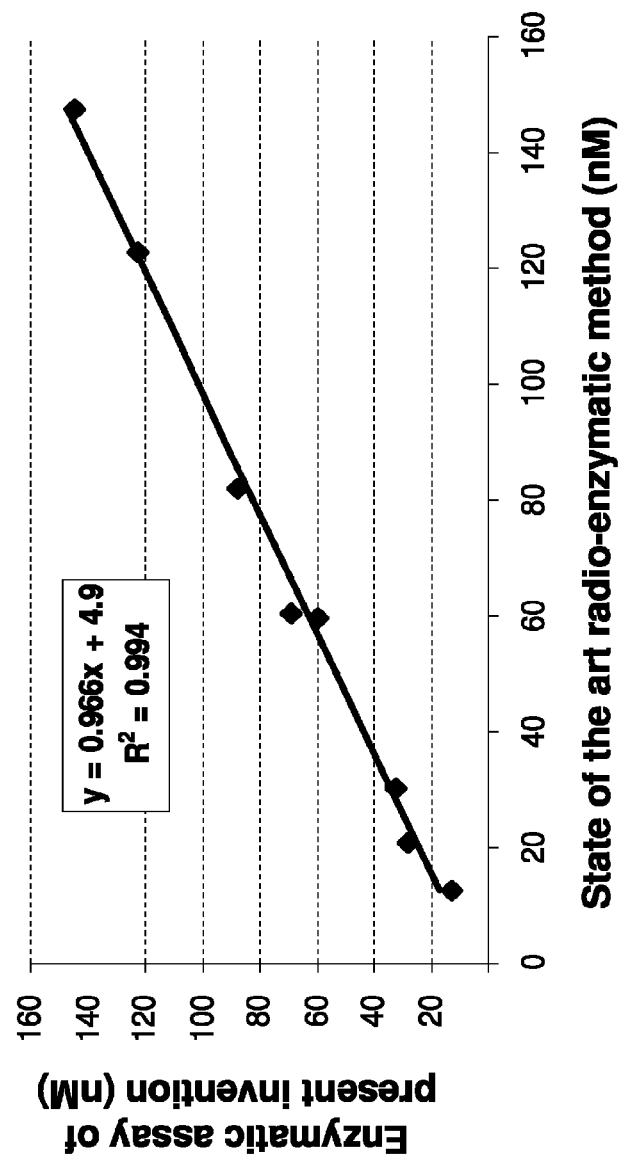

FIG. 9 shows the results of the determination of Vitamin B6 in serum and plasma samples by the method of the present invention and the correlation to the current state of the art method.

Figure 10:
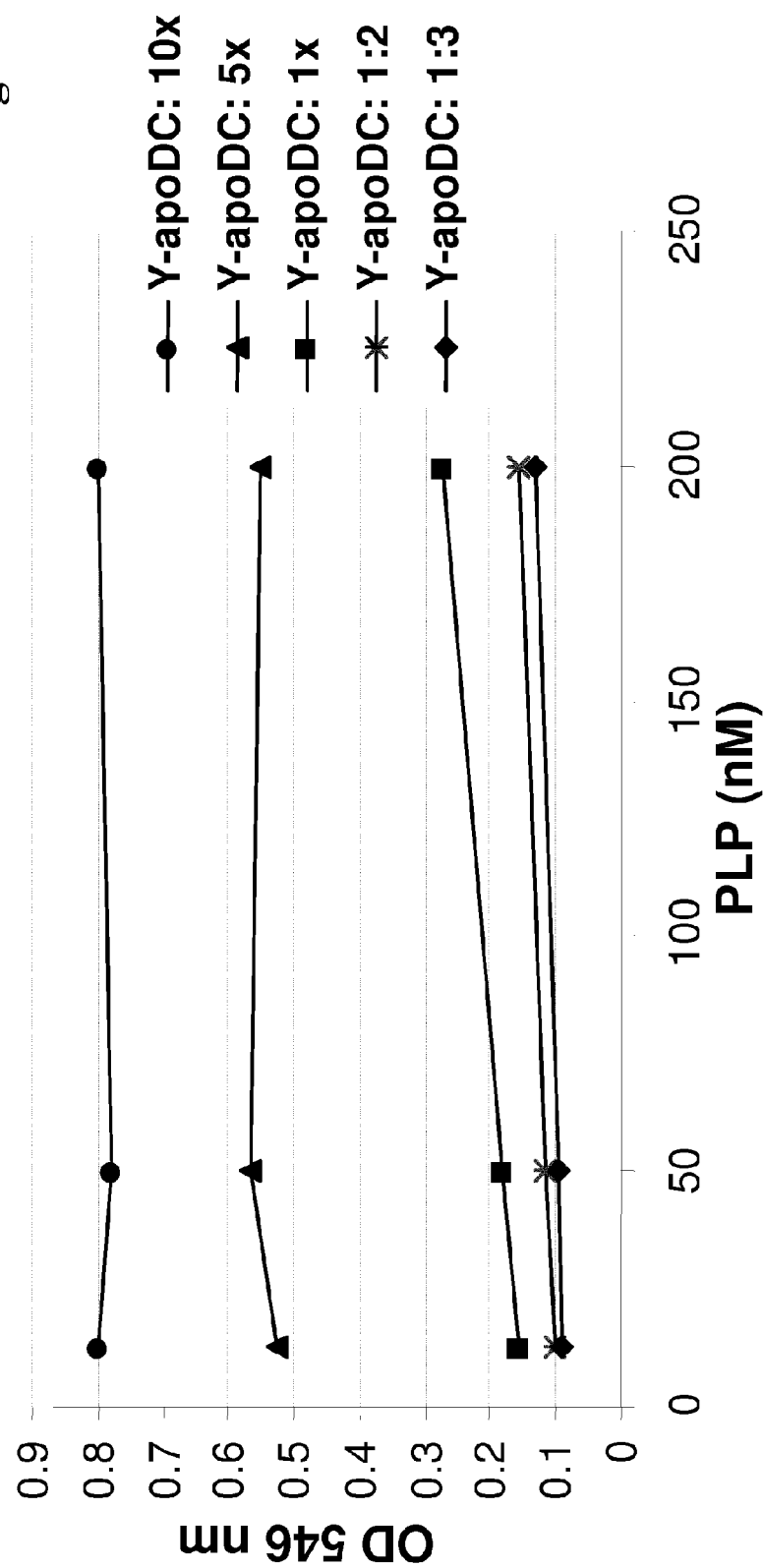

FIG. 10 shows the effects of different concentrations of tyrosine apo-decarboxylase enzyme prepared from crude bacterial extract using a 20-minutes assay protocol.

Figure 11:
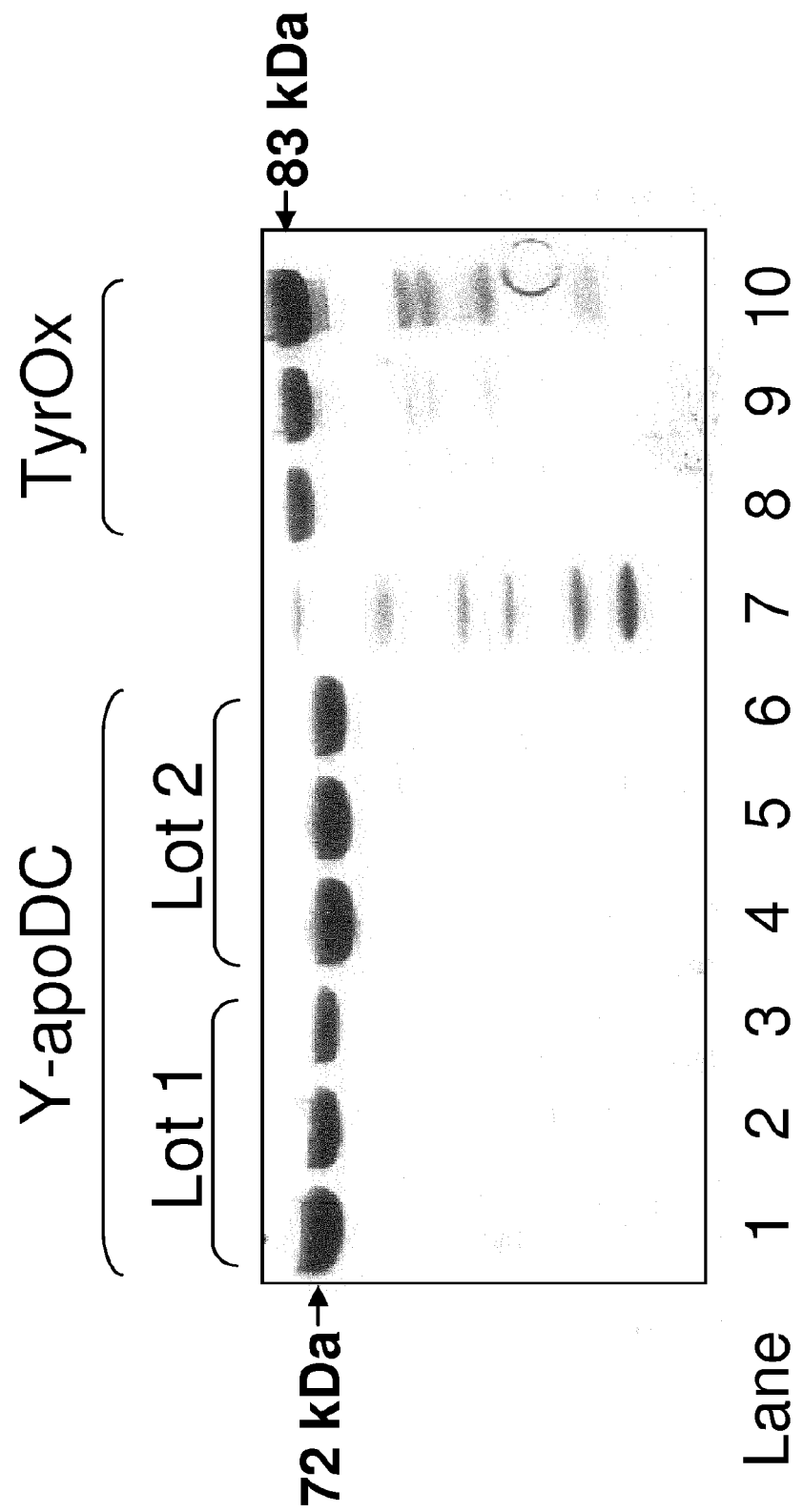

FIG. 11 shows a SDS-PAGE with highly purified, recombinant tyrosine apo-decarboxylase (Y-apoDC; 2 different batches) and tyramine oxidase (TyrOx) enzymes. Lanes 1, 4, 10: 20 µg of protein loaded; Lanes 2, 5, 9: 10 µg of protein loaded; Lanes 3, 6, 8: 5 µg of protein loaded; Lane 7: protein size marker (BioRad, Reinach, Switzerland).

Figure 12:
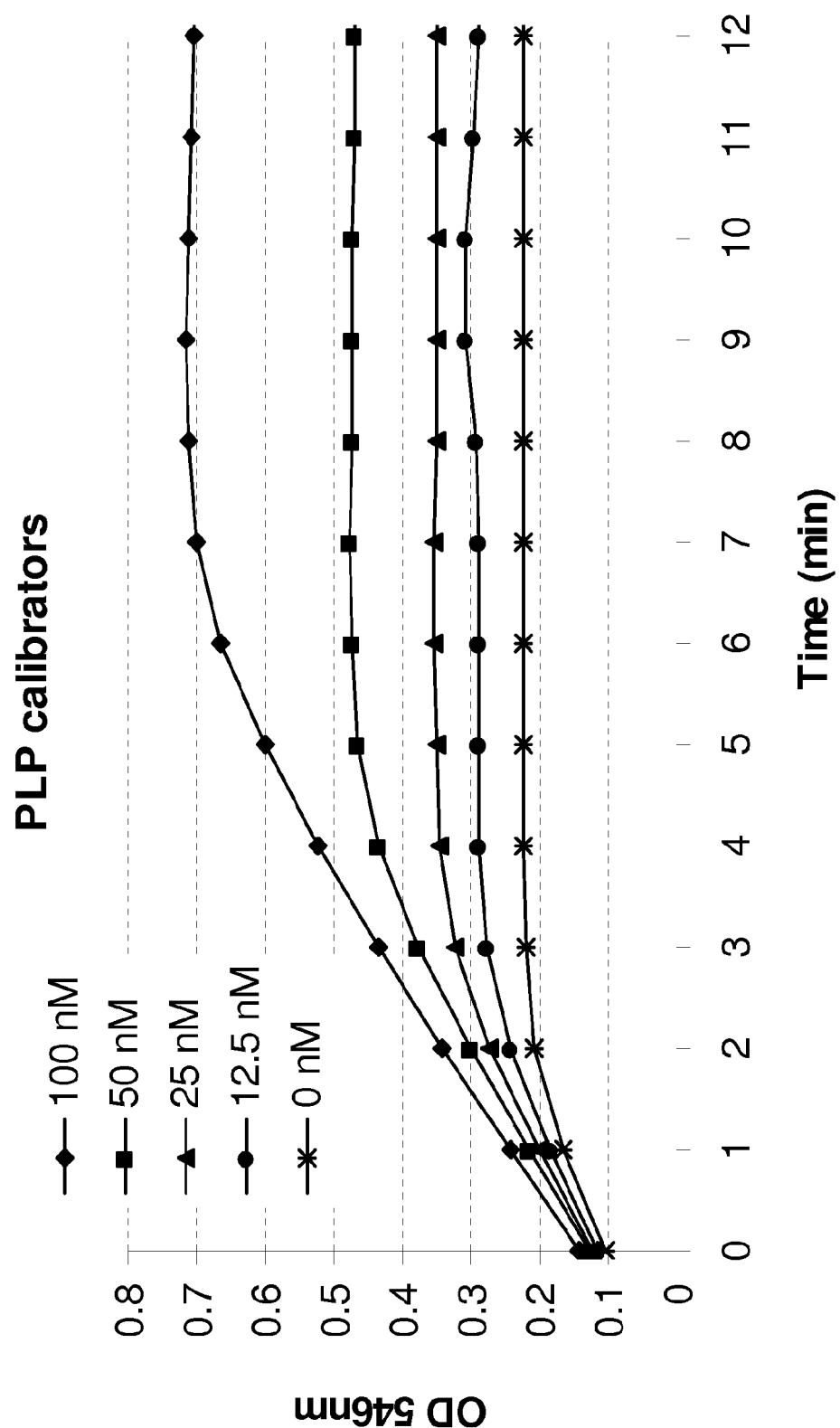

FIG. 12 shows the results of a kinetic experiment of the colorimetric reaction with calibrators using the method of the present invention.

Figure 13:
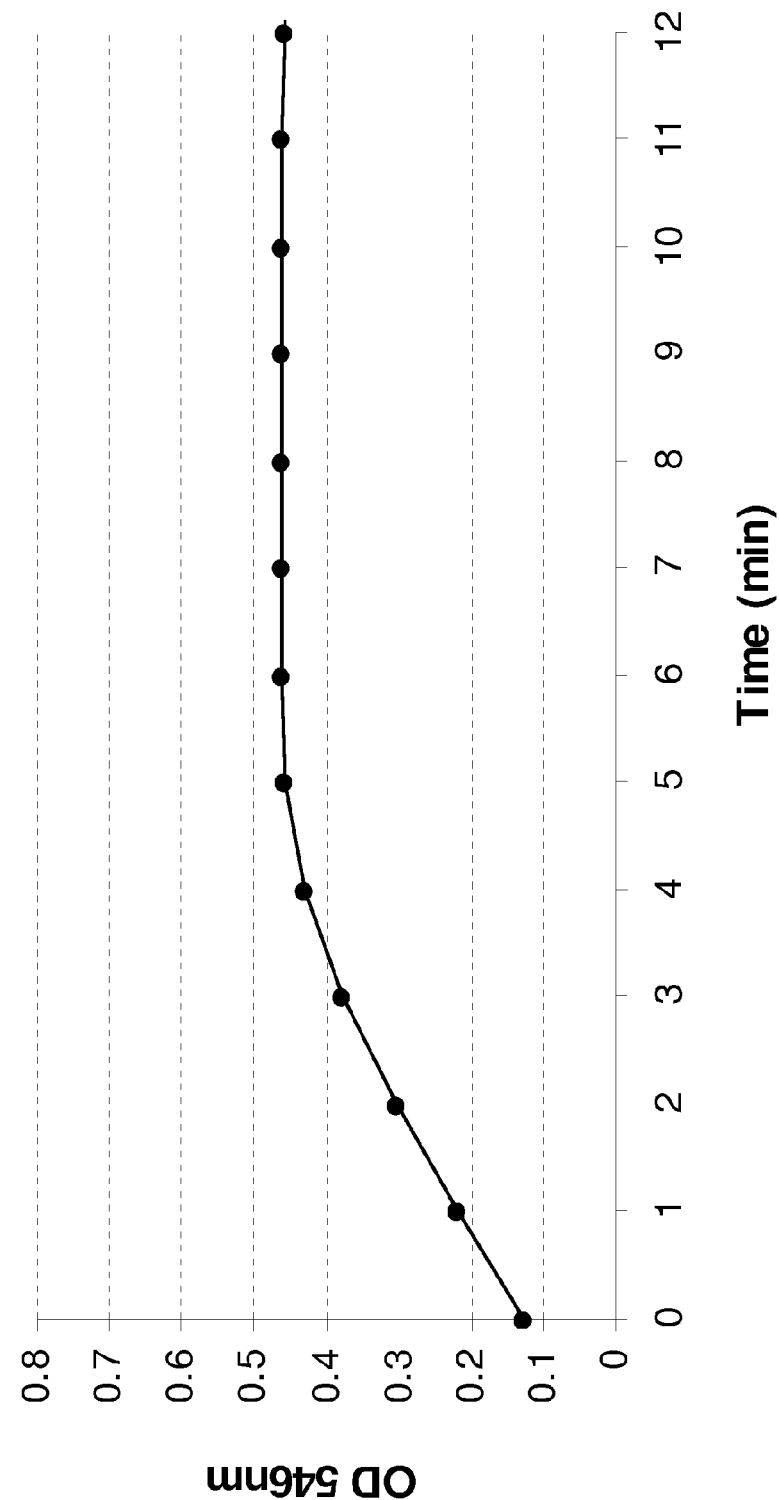

FIG. 13 shows the results of a kinetic experiment of the colorimetric reaction with an EDTA plasma sample using the method of the present invention.

Figure 14:
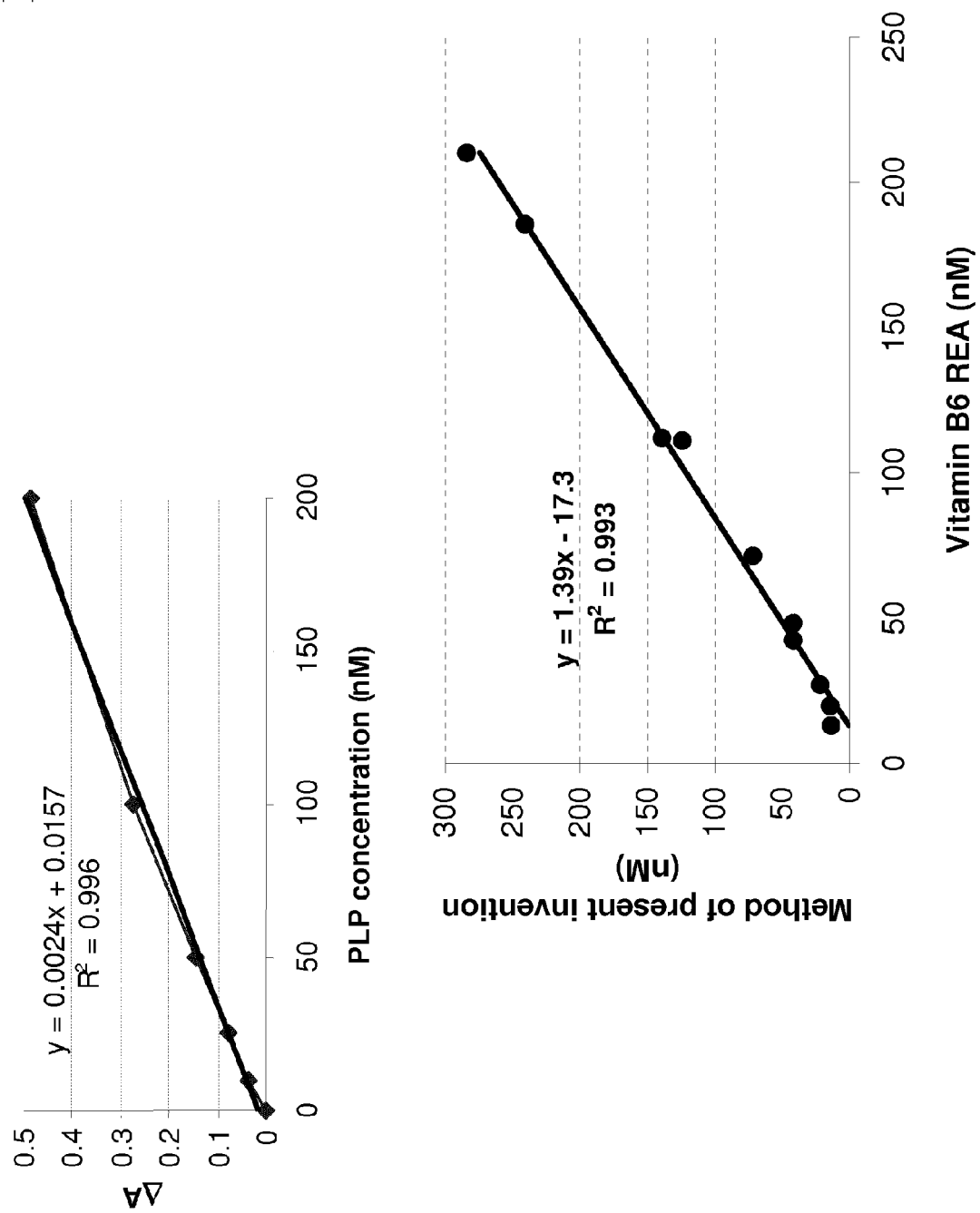

FIG. 14, upper part, shows the standard curve using a 20-minutes test protocol of the method of the present invention adapted to the Cobas Mira Plus analyzer. The lower part shows a correlation of results between the 20-minutes assay protocol adapted to the Cobas Mira Plus analyzer and the state of the art radioenzymatic method, the Vitamin B6 REA from Bühlmann Laboratories (Allschwil, Switzerland).

Figure 15:
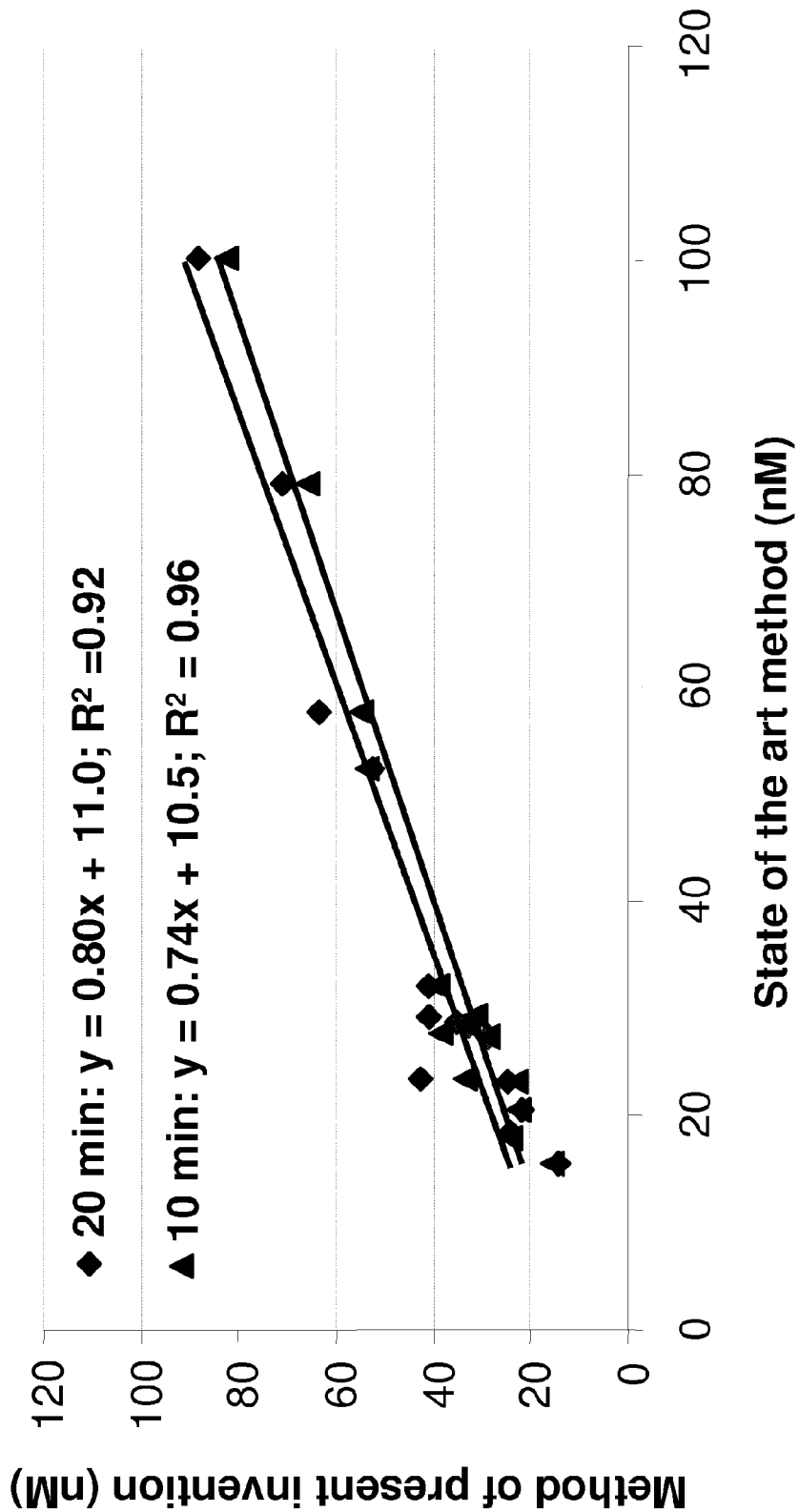

FIG. 15 shows the results of the determination of Vitamin B6 in 14 serum and plasma samples by the method of the present invention with reduced incubation times (20 vs 10 minutes) suitable for the Konelab T30 autoanalyzer and the correlation to the current state of the art radioenzymatic method.

Figure 16:
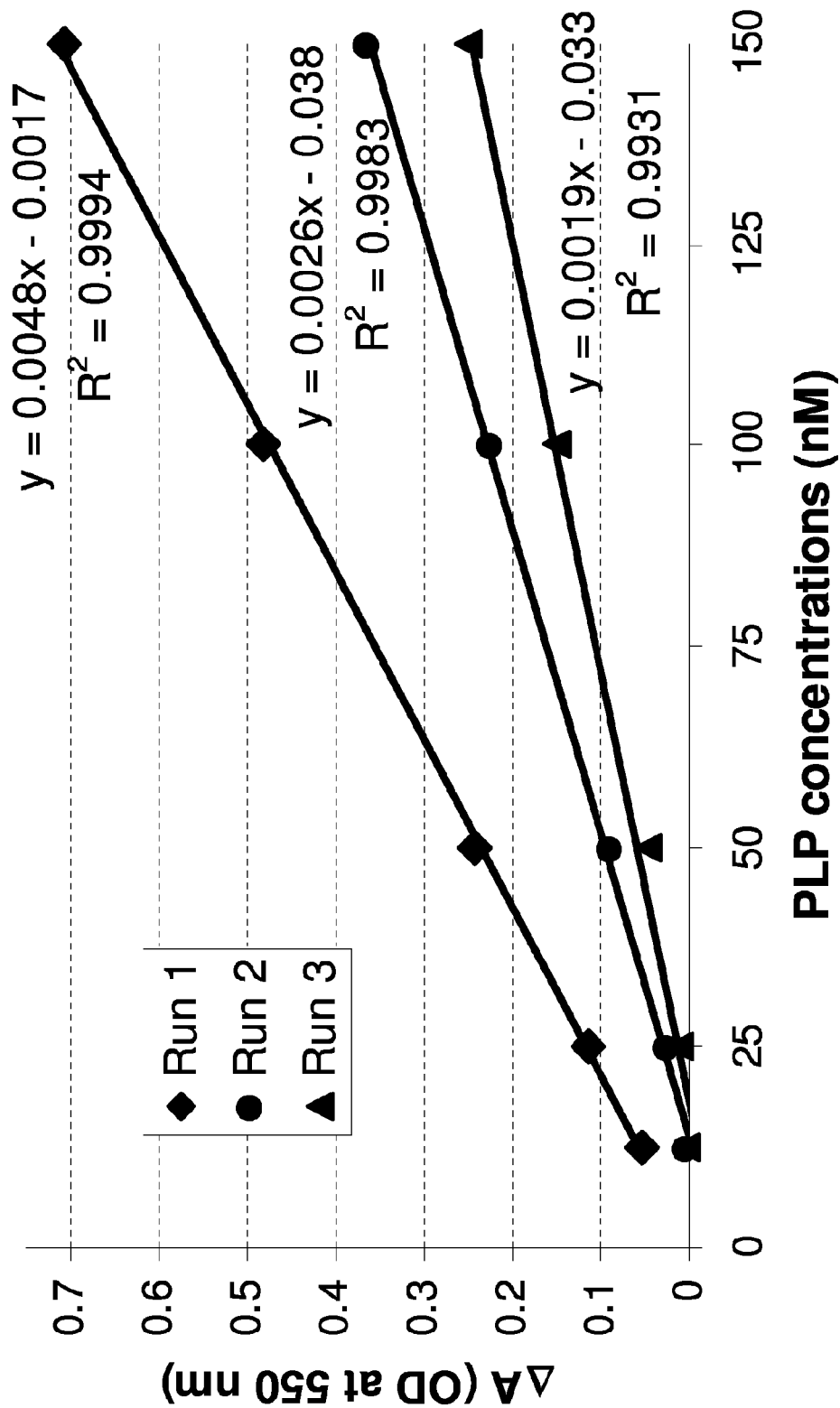

FIG. 16 shows the data of three standard curves using an 8-minutes test protocol of the method of the present invention adapted to the Cobas Mira Plus analyzer. Run 1, 2, and 3, respectively, represent three different assay conditions as described in Table 4 of Example 8.

Figure 17:
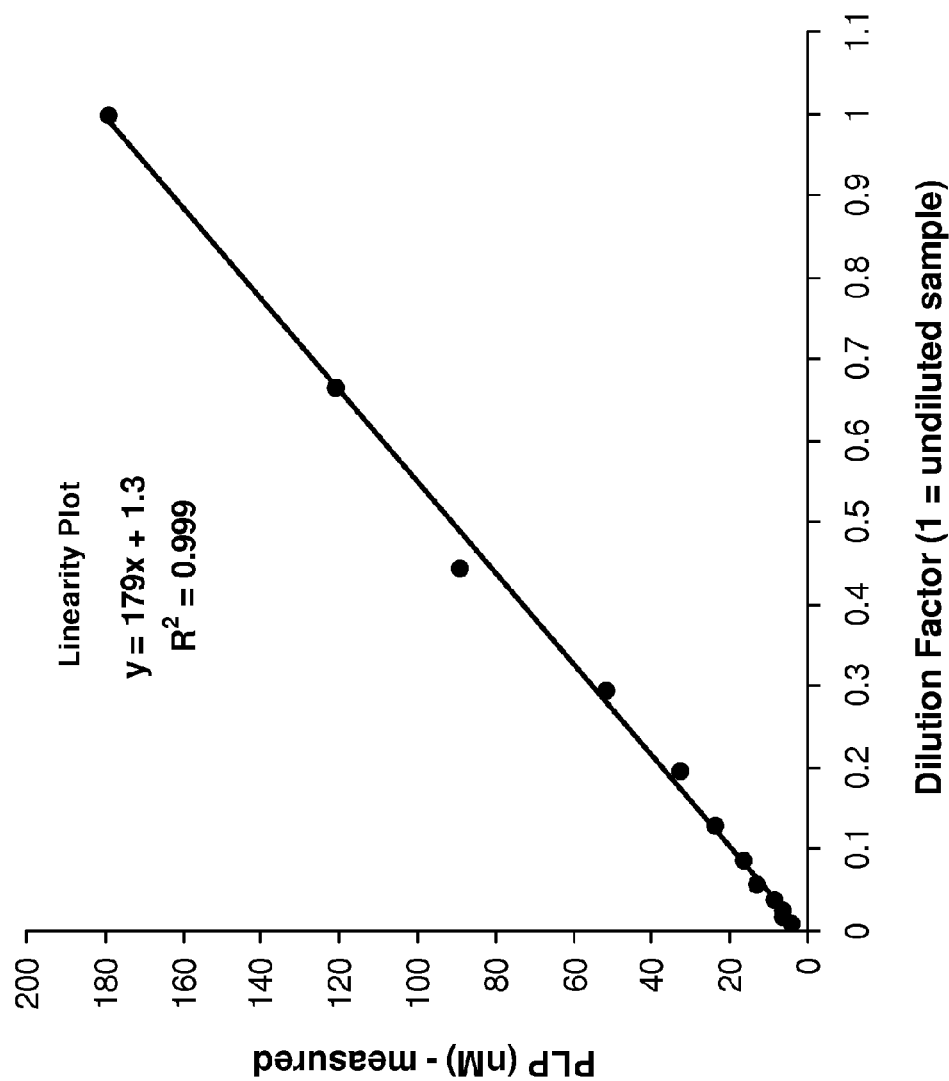

FIG. 17 shows the linearity of the method of the present invention using recombinant enzymes.

Figure 18:
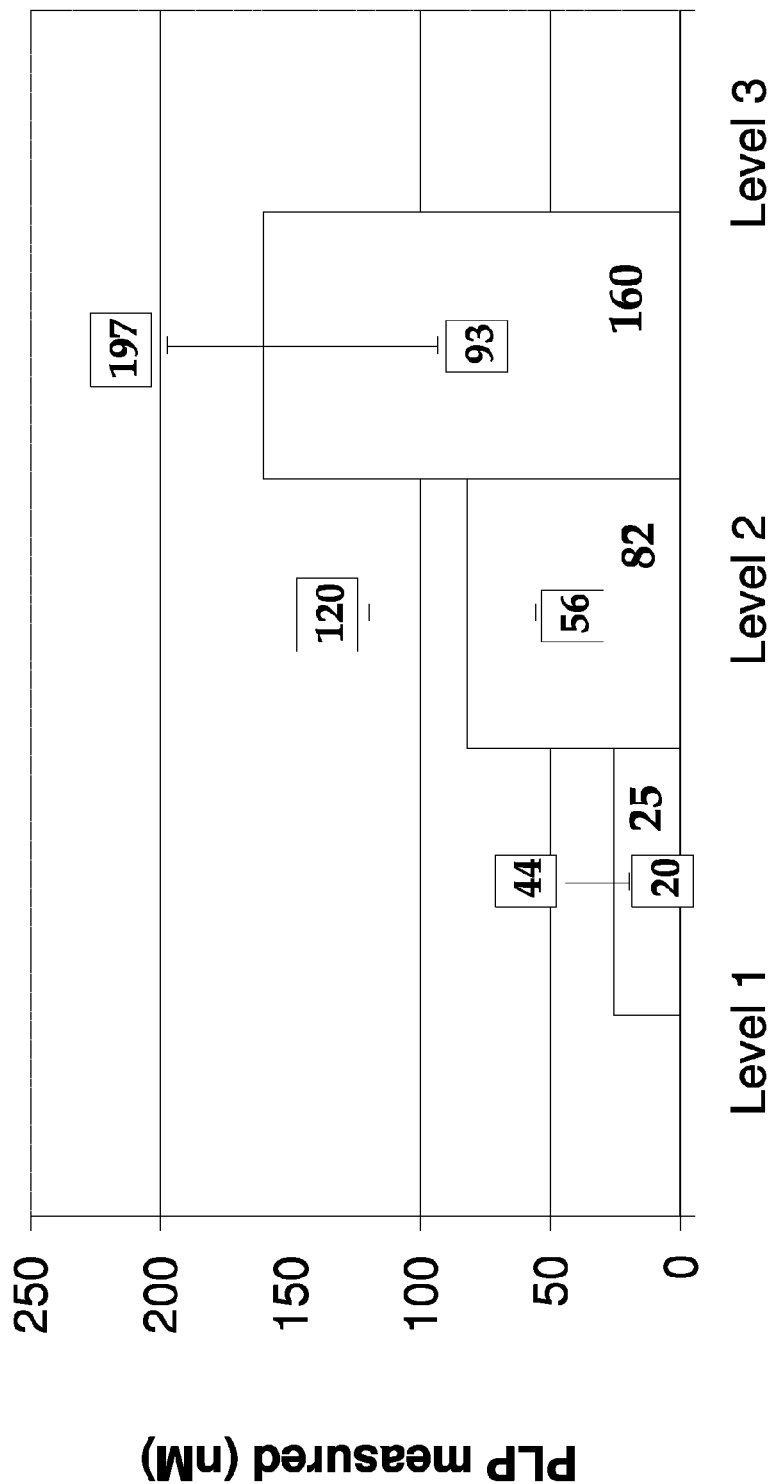

FIG. 18 shows the results of the determination of vitamin B6 in external Quality Controls for the validation of the method of the present invention using recombinant enzymes. Columns, the measured values (bold numbers) using the method of the present invention; bars with framed numbers, expected range as per manufacturer of the Quality Controls.

Figure 19:
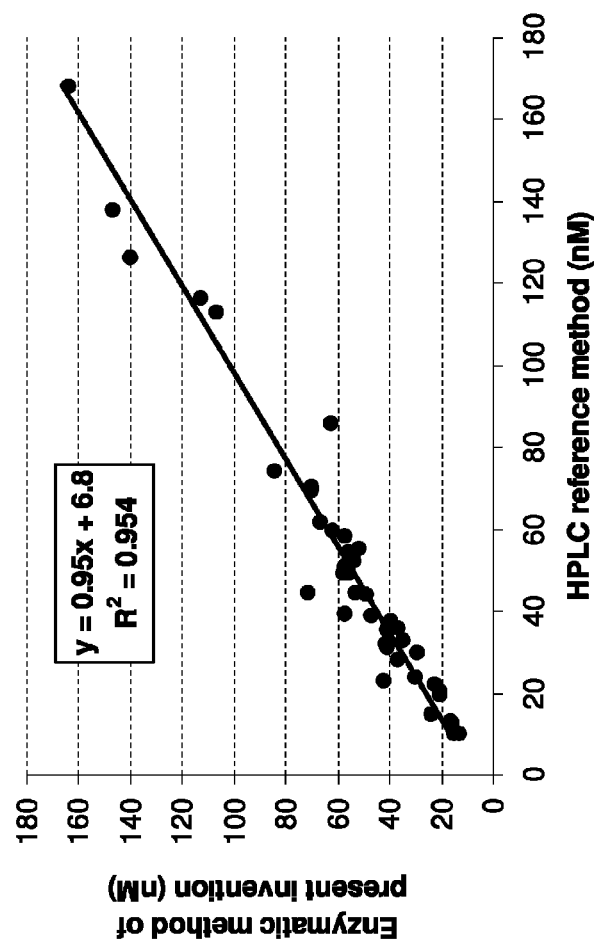

FIG. 19 shows an extended correlation of EDTA plasma samples measured by the method of the present invention using recombinant enzymes and a HPLC reference method.

EXAMPLES

Example 1

Measurement of PLP in Buffer Solution (Standardisation)

The assay principle is shown in FIG. 2. In this assay, the PLP-specific reaction is catalyzed by the tyrosine-specific enzyme Y-apoDC (EC 4.1.1.25) which converts tyrosine to tyramine. The Y-apoDC activity strictly depends on PLP as co-factor (co-substrate). This first specific reaction is coupled with a fully enzymatic colorimetric reaction. Briefly, the tyramine produced in the first reaction is oxidized to p-hydroxybenzyl aldehyde, ammonia ($NH_3$) and hydrogen peroxide ($H_2O_2$) by the action of TyrOx (EC 1.4.3.6). In the presence of peroxidase (EC 1.11.1.7; e.g. horse radish peroxidase [HRP]), $H_2O_2$ catalyzes the reaction of 4-aminoantipyrine (4-AAP), the hydrogen donor, and N-ethyl-N-(2-hydroxy-3-sulfopropyl)-m-toluidine (TOOS), the oxygen acceptor, to quinoneimine (a purple dye) whose absorbance (optical density, OD) is then monitored at 546 nm.

Standard assay conditions were: PLP (Fluka, Buchs, Switzerland) was dissolved into acetate buffer (250 mM, pH 5.5) to obtain a stock solution of 4 mM. A PLP standard curve from 12.5 nM to 200 nM was prepared by adding 50 µl of correspondingly diluted PLP solutions and 50 µl of a 2 mM L-tyrosine (Fluka, Buchs, Switzerland) solution in acetate buffer (250 mM, pH 5.5) to 50 µl Tyrosine Apodecarboxylase (0.15 U/mL; Sigma, St. Louis, USA) in acetate buffer (250 mM, pH 5.5). The reaction mixture was incubated for 90 minutes at 37° C. The reaction was stopped by adding 50 µl of a 3 mM 4-AAP (Sigma, St. Louis, USA) solution in Tris-HCl buffer (900 mM, pH 7.8). The colour reaction was then started by adding 50 µl of a solution containing 25 mM TOOS (Fluka, Buchs, Switzerland), 0.2 U/mL Tyramine Oxidase (Sigma, St. Louis, USA) and 10 U/mL Horseradish Peroxidase (Sigma, St. Louis, USA) in Tris-HCl buffer, pH 7.8. After 30 minutes incubation at 37° C. the purple-coloured reaction product quinoneimine was measured at a wavelength of 546 nm. The intensity of the absorbance of quinoneimine is directly proportional to the amount of PLP present in the sample. The absorbance is linear over the range of <10 to 200 nM of PLP as shown in FIG. 3 ($R^2=0.997$). This assay was set up in a Nunc F8 MAXISORP microplate (Nunc/Thermo Fisher Scientific, Roskilde, Denmark) and incubated and measured in a VERSAmax microplate reader from Molecular Device (Bucher biotec, Basel, Switzerland).

Example 2

Optimizing the L-Tyrosine Concentration

The standard assay conditions of Example 1 were used, but the concentration of L-Tyrosine was varied between 0.4 and 2 mM. The results are shown in FIG. 4. 2 mM L-Tyrosine was the optimum substrate concentration for the assay of the present invention.

Example 3

Optimizing the Colour Reaction

In order to optimize the colour reaction with the enzyme horseradish peroxidase, different oxygen acceptors (the colorizing agents, all at 25 mM) were tested for the reaction with the hydrogen donor, 4-AAP (fixed at 3 mM), catalyzed by hydrogen peroxide, the latter directly proportional to the amount of PLP present in the calibrators (samples). Two highly active colorizing agents were found, TOOS (N-ethyl-N-(2-hydroxy-3-sulfopropyl)-m-toluidin) and DHBS (3,5-dichloro-2-hydroxybenzenesulphonate) whereas TBHB (3-hydroxy-2,4,6-tribomobenzoic acid) and VA (vanillic acid) were only slightly reactive (see FIG. 5). Using the standard assay conditions as described in Example 1, 2.5 mM as well as 25 mM of TOOS yielded the same strong coloration, whereas lower concentrations of DHBS showed clearly reduced reactivity (see FIG. 6). Hence, TOOS was chosen and fixed at a concentration of 25 mM for any further experiments using the standard assay conditions of the present invention.

Example 4

Optimizing Incubation Times

From the state of the art literature it was known that the first enzyme reaction using the tyrosine apo-decarboxylase (Y-apoDC) is the rate limiting step. Thus, the first incubation of the standard assay procedure as described in Example 1 was varied from 15 to 90 min, whereas the second incubation (the colorimetric reaction) was kept at 5 min. Interestingly, a plateau was reached around 0.3 absorbance units (OD at 546 nm) independent from the incubation time applied (see FIG. 7), suggesting that there must also be other limiting factors present. However, when the incubation time of the second reaction was increased to 30 min, the assay system behaved as expected and did not show any limitation in OD signal output (see FIG. 8). Hence, incubation times of 90 and 30 mins for the first and the second incubation, respectively, were chosen for any further experiments using the standard assay conditions of the present invention, at least when a microtiter plate assay was employed.

Example 5

Measurement of PLP in Serum and Plasma Samples with the Method of the Present Invention and Correlation of the Obtained Results with the State of the Art Method Four human serum and EDTA plasma samples each were diluted 1:40 in acetate buffer and then determined using the method of the present invention as described in Example 1 and with the state of the art radio-enzymatic method (see Instruction for Use of the BÜHLMANN Vitamin B6 REA, order code: RK-VB6; Bühlmann Laboratories AG, Allschwil, Switzerland), respectively. The correlation data are shown in FIG. 9, and it can be concluded therefrom that serum as well as plasma samples can be reliably measured with the method of the present invention over the entire standard range of the assay.

Example 6

Optimizing Enzyme Production (Synthesis of Recombinant Enzymes) for a Rapid Assay Protocol It was also attempted to speed up the method of the present invention as outlined in Example 1 in terms of incubation times to establish this method on autoanalyzers which often allow a maximum incubation time of 20 minutes only, some even less than 10 minutes. Thus, the final goal was to establish an 8-minutes assay protocol.

First experiments using the protocol as described in Example 1, but employing shorter incubation times of 15 min for the first enzyme reaction and 5 min for the second colorimetric reaction, respectively, led to very low signal outputs (see FIG. 10; Y-apoDC undiluted [1×], 1:2 or 1:3 diluted with acetate buffer). Thus, the concentration of the enzyme tyrosine apo-decarboxylase (Y-apoDC) was increased, but with the effect that the noise and the unspecific blank values, respectively, increased dramatically without generating any standard curve (see FIG. 10; Y-apoDC, 5-times [5×] and 10-times [10×] concentrated). A similar effect was observed when the concentration of the enzyme tyramine oxidase was increased. The reason for this was most probably due to nature of the two enzymes as they were prepared from crude bacterial extracts (both from Sigma, St. Louis, USA). Thus, highly purified enzymes were necessary for a faster and more sensitive assay. Therefore, recombinant enzymes were synthesised from the corresponding gene sequences of *Enterococcus feacalis* for Y-apoDC and of *E. coli* or *Arthrobacter* sp. for TyrOx, respectively.

Briefly, the coding frame of the corresponding *Enterococcus feacalis* (accession number AAM46082) gene of the tyrosine apo-decarboxylase (1860 bp, 620 aa) was generated according to the reference sequence UniProtKB/TrEMBL: Q59104 by DNA synthesis (Genscript, Piscataway, USA) and amplified by Taq DNA polymerase-involving PCR (Invitrogen AG, Basel, Switzerland). The amplification product was directly ligated into expression vector pBAD containing an araB promotor and a N-terminal extended $His_{12}$-tag (Invitrogen AG, Basel, Switzerland) according to the manufacturer's recommendations. The cDNAs of the tyramine oxidase (EC 1.4.3.6) were cloned and expressed from *Escherichia coli* K-12 strain (accession number NP_415904; 2178 bp, 726 aa) and from *Arthrobacter* sp. (accession number YP_832977; 1923 bp, 641). The cDNAs were obtained by PCR of isolated *E. coli* and *Arthrobacter* sp. genomic DNA, respectively, from lysed cell cultures using simple phenol:chloroform extraction and ethanol precipitation. The PCR-derived cDNAs for tyramine oxidase were also cloned into the arabinose-inducible *E. coli* expression vector pBAD. The three different expression vectors were transfected into *E. coli* XL10-Gold cells (Stratagene, USA) and incubated over night. Single colonies were selected, grown for 4-8 hrs in test cell cultures (5-100 ml), then induced with arabinose and grown for another 8-16 hrs. The obtained whole-cell samples were run on SDS-PAGE and stained by Coomassie Blue to directly identify clones which express the corresponding proteins in large amounts. Plasmids from positive cell cultures were selected, isolated and sequenced entirely to ensure their authenticity and entity of the cloned cDNAs. TOP10 *E. coli* cells (Invitrogen AG, Basel, Switzerland) were then transfected with the positive plasmids, and clones thereof were expanded for a few hours into 4-10 liter batch cultures at 37° C. using rich 2-YT medium supplemented with glycerol, ammonium acetate and potassium phosphate, then induced by 0.1% arabinose and grown overnight at 28-30° C. The cells were harvested by centrifugation and frozen at −80° C. The yields were 15 gram frozen wet cell weight per liter of culture. For protein purification, 50 grams of cells were thawed directly into 500 ml of lysis buffer, where cells were efficiently disrupted by lysozyme, DNase and detergent activities. Soluble fractions are then separated from insoluble fractions by high-speed centrifugation. The soluble protein fractions were directly applied to a nickel chelate affinity column (GE Healthcare Europe GmbH, Glattbrugg, Switzerland), and the column was washed with high-salt buffers containing detergents and up to 120 mM imidazole. Then the bound proteins were eluted with 400 mM imidazole, desalted with a Sephadex G-25 column (GE Healthcare Europe GmbH, Glattbrugg, Switzerland) and stored as small aliquots at −80° C. The protein concentrations were determined with the DC Protein assay using BSA as standard (Bio-Rad, Reinach, Switzerland), and their purities were characterised by SDS-PAGE (see FIG. 11). Both recombinant enzymes showed homogenity, the expected protein size of 72 and 83 kDa, respectively, and purities above 95%. The protein yields were 60 up to 350 mg of purified enzyme per 4-10 liter batch.

Example 7

A Short 20-Minutes Protocol for an Autoanalyzer, Exemplary Standard Curve and Correlation to the State of the Art Method The use of the highly purified, recombinant enzymes from Example 6 allowed to markedly reduce the assay times without loosing (too much) signal output and sensitivity of the method of the present invention.

First, a kinetic experiment of the second (colorimetric) reaction confirmed that the maximal signal was reached after 8 minutes latest for the calibrators (pure PLP; see FIG. 12) as well as for an EDTA plasma sample (see FIG. 13), which was not achievable with crude enzyme preparations as used for the former experiments (cf. FIG. 7 vs 8). The assay conditions were the same as described in Example 1 except 40 µg of recombinant TyrOx instead of 10 mU of crude enzyme preparation was used per reaction. The first (specific) reaction with Y-apoDC (1.5 µg recombinant enzyme per reaction) was kept at 15 min, and this experiment was set up in a microtiter plate. Knowing that an assay using recombinant TyrOx needed a few minutes only for the completion of the colorimetric reaction, a 20-minutes assay protocol for the Cobas Mira Plus analyzer (Roche, Basel, Switzerland) was established. The test protocol for the method of the present invention adapted to the Cobas Mira Plus analyzer is illustrated in Table 1 and consisted of 3 reagents (R1, R2, R3) and of two incubation steps (specific reaction for 15 min, cycle 1 to 37; colorimetric reaction for 5 min, cycle 38 to 50; 1 cycle corresponds to 25 sec).

TABLE 1

20-minutes assay protocol for the Cobas Mira Plus analyzer

| Reagents | |
|---|---|
| R1 | Acetate buffer (pH 5.5) containing 2 mM L-tyrosine and 15 µg/ml Y-apoDC |
| R2 | Tris-HCl buffer (pH 8.0) containing 25 mM TOOS |
| R3 | Tris-HCl buffer (pH 8.0) containing 3 mM 4-AAP, 814 µg/ml TyrOx and 10 U/ml HRP |
| Protocol | (Instrument settings) |
| Cycle 1 | 100 µl R1<br>50 µl calibrator or sample (prediluted 1:40 in acetate buffer) |
| Cycles 2-36 | Incubation at 37° C. |
| Cycle 37 | 50 µl R2 |
| Cycle 38 | 50 µl R3 (start of color measurement) |
| Cycles 39-50 | Incubation at 37° C. |
| Measurement | OD is monitored during the 5-minutes color reaction (cylces 39-50). Results are expressed as the net absorbance between the first OD reading (at cycle 39) and last OD reading (at cycle 50). |

An exemplary standard curve and correlation data between the short 20-minutes version of the method of the present invention and the state of the art method (Vitamin B6 REA; Bühlmann Laboratories, Allschwil, Switzerland) are shown in FIG. 14. The net signal output (ΔA) was unexpectedly high yielding approximately 0.5 OD, and the correlation of 10 serum and EDTA plasma samples was excellent ($R^2=0.993$).

Example 8

Towards an 8-Minutes Assay Protocol of the Method of the Present Invention Adapted for Autoanalyzers In the next step, it was attempted to reduce the test time to 10 minutes only. The experiments were done on a Konelab T30 instrument (Thermo Fisher Scientific, Vantaa, Finland). The general assay conditions were the same as described in Example 7 including reagents R1, R2 and R3, respectively, except that the samples (S) were prediluted with acetate buffer at 1:10 instead of 1:40. A 20-minutes, 14-minutes and 10-minutes assay protocol, respectively, were established and are detailed in Table 2.

TABLE 2

Protocols of the method of the present invention adapted to the Konelab T30 analyzer.

| Steps | 20 min | 14 min | 10 min |
|---|---|---|---|
| R1 | 45 µl | 48 µl | 48 µl |
| S/Cal (1:10) | 20 µl | 12 µl | 12 µl |
| Short incub. | 25 sec | 25 sec | 25 sec |
| R2 | 70 µl | 70 µl | 70 µl |
| Specific react. | 850 sec | 610 sec | 380 sec |
| Blanking | yes | none | none |
| R3 | 115 µl | 120 µl | 120 µl |
| Short incub. | — | 25 sec | 25 sec |
| Colorim. react. | 300 sec | 180 sec | 170 sec |
| Read at 540 nm | | | |

Oppositely to the Cobas Mira Plus protocol (see Example 7), the colorimetric reading was done by a kinetic method and, therefore, the results are expressed as OD (measured at 540 nm) per minute. Typical data obtained with calibrators (Cal) are shown in Table 3.

TABLE 3

Typical standard curve data for a 20-, 14- and 10-minutes assay protocol, respectively.

| | OD 540 nm/min (kinetic reading) | | |
|---|---|---|---|
| PLP (nM) | 20 min | 14 min | 10 min |
| 12.5 | 0.012 | 0.018 | 0.011 |
| 50 | 0.042 | 0.032 | 0.017 |
| 200 | 0.221 | 0.107 | 0.046 |

PLP levels in 14 EDTA plasma samples were determined with the 10- and the 20-minutes protocol of the method of the present invention adapted to the Konelab T30 analyzer and correlated to the results obtained with the state of the art method, the vitamin B6 REA (see FIG. 15). These results show that the method of the present invention allow reliable PLP determinations in biological samples even when the total assay time was reduced to 10 minutes.

Finally and unexpectedly, it was possible to reduce the test time of the method of the present invention even further to as low as 8 minutes when adapted to the Cobas Mira Plus autoanalyzer (Roche, Basel, Switzerland) by fine-tuning the assay conditions as described above in Table 1 of Example 7. The reagent volumes and concentrations, respectively, as well as the incubation cycles were titrated (see Table 4), and it was found that standard curves with sufficient signal output (in terms of net OD values) could be generated with all three conditions presented (see FIG. 16). The curve was particularly well when the Y-apoDC concentration was increased from 1.5 to 12.5 µg/reaction (Run 1).

TABLE 4

Assay conditions of the 8-minutes assay protocol of the method of the present invention adapted to the Cobas Mira Plus analyzer (1 cycle corresponds to 25 sec).

| Steps | Reagent | Run 1 | Run 2 | Run 3 |
|---|---|---|---|---|
| Start | 70 µl R1 (L-Tyrosin/4-AAP) | 10 mM/ 0.8 mM | 10 mM/ 0.8 mM | 10 mM/ 0.8 mM |
|  | 70 µl R2 (Y-apoDC) | 12.5 µg | 1.5 µg | 1.5 µg |
|  | Calibrator | 3 µl | 2 µl | 2 µl |
| 1$^{st}$ Inc. | Incubation at 37° C. | Cycle 1-12 | 1-13 | 1-13 |
|  | 100 µl R3 (TyrOX/HRP/TOOS) | 40.7 µg/ 10U/10 mM | 40.7 µg/ 10U/10 mM | 40.7 µg/ 10U/10 mM |
| 2$^{nd}$ Inc. | Incubation at 37° C. | Cycle 13-19 | 14-19 | 14-19 |
| Measur. | Endpoint at 550 nm |  |  |  |

Example 9

Recovery and Linearity

The microtiter plate version of the method of the present invention as having been used in Examples 1 to 5 was further validated, but using the recombinant Y-apoDC enzyme. The assay protocol of Example 1 was changed as follows: 0.6 µg recombinant Y-apoDC instead of 7.5 mU crude extract and 4.4 µg TyrOx instead of 10 mU were used per reaction, and the incubation times of the first and second incubation were set to 60 and 30 minutes, respectively.

One EDTA plasma sample containing a low level of PLP (22.5 nM) was spiked with increasing concentrations from a PLP stock solution and the spiked samples were diluted 1:40 in acetate buffer and then measured with the method of the present invention as described above. The recoveries are shown in Table 5 and yielded a mean recovery (observed vs expected concentration) of 103%.

TABLE 5

Spiking recovery

| Sample | nM | Spiked with [nM] | Observed [nM] | Expected [nM] | O/E [%] |
|---|---|---|---|---|---|
| EDTA-plasma 1 | 22.5 | 105 | 130.9 | 127.8 | 102 |
|  |  | 53 | 78.1 | 75.2 | 104 |
|  |  | 26 | 49.9 | 48.8 | 102 |
|  |  | 13 | 36.6 | 35.7 | 103 |

Two EDTA plasma samples containing high levels of PLP were further diluted with acetate buffer and the spiked samples were measured with the method of the present invention as described above. As an example, the linearity graph of the sample 1 is shown in FIG. 17. The assay of the present invention is linear over the entire standard range (from 10 to at least 180 nM) and yielded a mean difference (observed vs expected concentration) of 3% only (Table 6).

TABLE 6

Dilution linearity

|  | Dilution | Observed [nM] | Expected [nM] | O/E [%] |
|---|---|---|---|---|
| EDTA Plasma 1 | 1:1 | 179.0 | 179.0 |  |
|  | 1:1.5 | 120.9 | 119.3 | 101 |
|  | 1:2.25 | 88.8 | 79.5 | 112 |
|  | 1:3.37 | 51.6 | 53.0 | 97 |
|  | 1:5.06 | 32.5 | 35.4 | 92 |
|  | 1:7.59 | 23.5 | 23.6 | 100 |
|  | 1:11.39 | 15.9 | 15.7 | 101 |
|  | 1:17.09 | 12.7 | 10.5 | 121 |
|  | Mean |  |  | 103 |
| EDTA Plasma 2 | 1:1 | 173.2 | 173.2 |  |
|  | 1:1.5 | 118.0 | 115.5 | 102 |
|  | 1:2.25 | 77.6 | 77.0 | 101 |
|  | 1:3.37 | 50.6 | 51.3 | 99 |
|  | 1:5.06 | 36.1 | 34.2 | 106 |
|  | 1:7.59 | 23.1 | 22.8 | 101 |
|  | 1:11.39 | 16.3 | 15.2 | 107 |
|  | 1:17.09 | 10.9 | 10.1 | 107 |
|  | Mean |  |  | 103 |

Example 10

Measurement of External Quality Controls for Vitamin B6

In order to further characterise the reliability and accuracy of the method of the present invention, external 3-level quality controls for vitamin B6 were analyzed. The Vitamin B1/B6 Quality Controls Level 1, 2, and 3, respectively, were reconstituted as described by the manufacturer (Eurotrol, Ede, The Netherlands), further diluted 1:40 with acetate buffer and measured by the method of the present invention as described in Example 9. The results of all 3 controls were found within the expected range and close to the target value as given by the manufacturer (see FIG. 18).

Example 11

Determination of Vitamin B6 (PLP) in Apparently Healthy Blood Donors

The normal distribution of vitamin B6 levels was assessed in EDTA plasma samples from 58 apparently healthy blood donors having donated their blood at the Swiss Red Cross Center in Basel, Switzerland (age: 18-70 years, sex equally distributed). The samples were diluted 1:40 in acetate buffer and then measured by the method of the present invention as described in Example 9. The distribution shown in Table 7 was as expected. Only one donor exhibited a vitamin B6 deficiency, whereas almost 75% of the donors showed vitamin B6 levels within the normal range between approximately 30 and 100 nM as described in the literature (e.g. Leklem J E. J Nutr 1990; 120:1503-7).

TABLE 7

Vitamin B6 levels of apparently healthy blood donors

| PLP | n |
|---|---|
| <20 nM | 1 |
| 20-30 nM | 0 |
| 30-40 nM | 11 |
| 40-100 nM | 32 |
| 100-200 nM | 11 |
| >200 nM | 3 |
| Total | 58 |

Example 12

Extended Correlation of EDTA Plasma Samples Measured with the Method of the Present Invention Using Recombinant Enzymes and a HPLC Reference Method Finally, 44 EDTA plasma samples covering the entire standard range were diluted 1:40 in acetate buffer and then measured with the method of the present invention as described in Example 9. For reference, the same samples were also measured with a High-Performance Liquid Chromatography (HPLC) method established at the University Hospital of Zurich, Institute of Clinical Chemistry (Jaworek and von Eckardstein, 2011). The data were correlated and are illustrated in FIG. 19. The correlation of the method of the present invention with a method of a higher order was excellent ($R^2$>0.95, slope 0.95) finally confirming the reliability and accuracy of this new method.

The invention claimed is:

1. A method for determining the concentration of pyridoxal-5'-phosphate (PLP, vitamin B6) in a sample, comprising the steps of
    a) incubating the sample containing PLP with at least one PLP-dependent tyrosine apo-decarboxylase,
    b) contacting the PLP-dependent enzyme(s) of step a) with tyrosine,
    c) enzymatically converting conversion of the tyrosine of step b) to tyramine using the tyrosine apo-decarboxylase,
    d) enzymatically converting the tyramine resulting from step c) to hydrogen peroxide and at least one other product using a tyramine oxidase,
    e) enzymatically reacting at least one indicator substrate and the hydrogen peroxide of step d) to form a compound detectable using a peroxidase,
    f) measuring the quantity of the detectable compound of step e)
    and
    g) determining the concentration of PLP in the sample based on the quantity of the detectable compound measured in step f) and measurements of the quantity of the detectable compound measured in step f) for known concentrations of PLP,
wherein
the enzymes of step a) and d) are produced, expressed and purified as recombinant enzymes and
the assay time is reduced in comparison with the same assay when using enzymes prepared from crude bacterial extracts in steps a) and c).

2. The method of claim 1, wherein the peroxidase is horseradish peroxidase.

3. The method of claim 1, wherein the enzymatic conversion of the hydrogen peroxide of step e) forms in the presence of at least one hydrogen donor and at least one oxygen acceptor a detectable compound.

4. The method of claim 3, wherein the hydrogen donor is selected from the group consisting of 4-AAP (4-aminoantipyrine), 4-AP (4-aminophenazone), o-phenylenediamine, TMB (3,3',5,5'-tetramethylbenzidine), MBTH hydrochoride (3-methyl-2-benzothiazolinonehydrazone hydrochloride hydrate), OPD (1,2-phenylenediamine), 4-aminoantipyrine hydrochloride, 5-aminosalicylic acid, and 5-amino-2-hydroxybenzoic acid, and the oxygen acceptor is chosen from the group of TOOS (N-ethyl-N-(2-hydroxy-3-sulfopropyl)-m-toluidin), ABTS (2,2'-azinobis (3-ethylbenzothiazoline-6-sulfonic acid), DCBS (4-chlorophenol; 3,5-dichloro-2-hydroxybenzensulfonic acid), DCHBS (3,5-dichloro-2-hydroxybenzenesulfomc acid), DHB (3,4-dihydroxybenzoic acid), DHBS (3,5-dichloro-2-hydroxybenzenesulphonate), HBS (p-hydroxy-benzene sulfonate), TBHBA (2,4,6-tribromo-3-hydroxybenzoic acid), TBHB (3-hydroxy-2,4,6-tribomobenzoic acid), HBA (4-hydroxybenzoic acid), EHSPT (N-ethyl-N-(2-hydroxy-3-sulfopropyl)-m-toluidine), Vanillic acid, Homovanillic acid, ESPA (N-ethyl-N-(3-sulfopropyl)m-anisidine), ADPS (N-Ethyl-N-(3-sulfopropyl)-3-methoxyaniline), ADOS (N-Ethyl-N-(2-hydroxy-3-sulfopropyl)-3-methoxyl aniline), TOPS (N-Ethyl-N-(3-sulfopropyl)-3-methylaniline), DAOS (N-ethyl-N-(2-hydroxy-3-sulfopropyl)-3,5-dimethoxyaniline), HDAOS (N-(2-Hydroxysulfopropyl)-3,5-dimethyoxyaniline), MADB (N,N-Bis(4-sulfobutyl)-3,5-dimethylaniline), MAOS (N-Ethyl-N-(2-hydroxy-3-sulfopropyl)-3,5-dimethylaniline), TODB (N,N-Bis(4-sulfobutyl)-3-methylaniline), ALPS (N-Ethyl-N-(3-sulfopropyl)aniline), DEA (N, N-diethylaniline), dimethylaniline, 3-diethylaminotoluene, N,N-diethyl-m-toluidine, N,N-diethyl-3-methylaniline, DMA (N,N-dimethylaniline), Phenol, Aminophenol, Indophenol, 4-chlorophenol, 2,4-DCP (2,4-dichlorophenol), 2,4,6-tribromophenol, guaiacol (2-methoxyphenol), Guaiac, Leucomalachite green, Nadi reagent, Phenolphtalein, Ferrocyanide, Adrenaline, DAB (3,3'-diamino-benzidine), di-anisidine (3,3'-dimethoxybenzidine), o-tolidine (3,3'-dimethyl-(1,1'-biphenyl)-4,4'-diamine), diphenylamine, o-toluidine (1-methyl-1,2-amino-benzene), m-toluidine (3-methylbenzenamine), p-toluidine (4-aminotoluene or 4-methylaniline), benzidine (4,4'-diaminobiphenyl), catechol (1,2-dihydroxybenzene), pyrogallol (1,2,3-trihydroxybenzene), o-cresol (2-hydroxy-1-methylbenzene), m-cresol (3-Methylphenol), p-cresol (4-Methylphenol), 4-methylcatechol (1,2-dihydroxy-4-methylbenzene), 4-diphenyl sulfonic acid, 2,6-dichloroindophenol, CN (4-chloro-1-napthol), alpha-naphthol, beta-naphthol 5-ASA (5-aminosalicylic acid), AEC (3-amino-9-ethylcarbazole), 5 amino-indole, 7 amino-indole, 5 amino-benzimidazole, 7 amino-benzimidazole, 5 amino-benzothiazole, 7 amino-benzothiazole, 5 amino-benzoxazole, 7 amino-benzoxazole, 5 amino-indazole, 7 amino-indazole, a combined reagent of tetravalent titanium compound and 5-Br-PAPS (2-(5-bromo-2-pyridylazo)-5-(N-propyl-N-sulfopropylamino)phenol) or Xylenol Orange (3,3'-Bis[N,N-bis(carboxymethyl)aminomethyl]-o-cresolsulfonephthalein tetrasodium salt) and the like.

5. The method of claim 4, wherein the hydrogen donor is 4-aminoantipyrine (4-AAP) and the oxygen acceptor is N-ethyl-N-(2-hydroxy-3-sulfopropyl)-m-toluidine (TOOS).

6. The method of claim 1, wherein the sample is selected from animal and human body fluids, tissue extracts, cell culture supernatants, extracts or solutions made from vegetables, meat, fish, cereals, flour, bread and other food products, food-related products, beverages, and dietary supplements.

7. The method of claim 6, wherein the sample is human serum or plasma.

8. The method of claim 1, wherein the quantity of the detectable compound is measured by spectroscopy at a wavelength between 200 nm and 1200 nm.

9. The method of claim 1, wherein the time for carrying out any of steps a) to f) is between 1 minute and 24 hours.

10. The method of claim 9, wherein the time for carrying out steps a) to c) is between 30 and 120 minutes and the time for carrying out steps d) to f) is between 5 and 60 minutes when used in a microtiter plate.

11. The method of claim 9, wherein the time for carrying out steps a) to c) is between 2 and 20 minutes and the time for carrying out steps d) to f) is between 1 and 10 minutes when used on an autoanalyzer.

12. The method of claim 1, wherein the pH of the reaction mixture in any of steps a) to f) is between pH 2 and pH 12.

13. The method of claim 12, wherein the pH of the reaction mixture of steps a), b) and c) is between pH 5 and 6, and the pH of the reaction mixture of steps d) and e) is between pH 6.5 and 8.5.

14. The method of claim 1, wherein the method is carried out at a temperature between 4° C. and 65° C.

15. The method according to claim 1, applied in a microtiter plate combined with a spectrophotometric or fluorimetric microtiter plate reader.

16. The method according to claim 1, applied in an autoanalyzer.

17. The method of claim 12, wherein the method is carried out at a temperature of 34° C. to 40° C.

* * * * *